US011931157B2

(12) United States Patent
Scharf et al.

(10) Patent No.: US 11,931,157 B2
(45) Date of Patent: *Mar. 19, 2024

(54) CARDIAC ANALYSIS USER INTERFACE SYSTEM AND METHOD

(71) Applicant: Acutus Medical, Inc., Carlsbad, CA (US)

(72) Inventors: Christoph Scharf, Horgen (CH); Graydon E. Beatty, Bloomington, MN (US); Gunter Scharf, Zurich (CH); Randell L. Werneth, Boise, ID (US); Timothy J. Corvi, Carlsbad, CA (US); J. Christopher Flaherty, Auburndale, FL (US); Maxwell R. Flaherty, Auburndale, FL (US)

(73) Assignee: ACUTUS MEDICAL, INC., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/578,522

(22) Filed: Jan. 19, 2022

(65) Prior Publication Data

US 2022/0386927 A1 Dec. 8, 2022

Related U.S. Application Data

(63) Continuation of application No. 15/128,563, filed as application No. PCT/US2015/022187 on Mar. 24, 2015, now Pat. No. 11,278,231.
(Continued)

(51) Int. Cl.
*A61B 8/12* (2006.01)
*A61B 5/00* (2006.01)
(Continued)

(52) U.S. Cl.
CPC .............. *A61B 5/339* (2021.01); *A61B 5/287* (2021.01); *A61B 5/6858* (2013.01);
(Continued)

(58) Field of Classification Search
CPC ...... A61B 18/1492; A61B 2018/00148; A61B 2018/00267; A61B 2018/00357;
(Continued)

(56) References Cited

U.S. PATENT DOCUMENTS 4,173,228 A 11/1979 Van Steenwyk et al.
4,841,977 A 6/1989 Griffith et al.
(Continued)

FOREIGN PATENT DOCUMENTS

CA 2825736 5/2008
CA 2829626 9/2012
(Continued)

OTHER PUBLICATIONS

He et al. "An equivalent body surface charge model representing three-dimensional bioelectrical activity" IEEE Transactions on Biomedical Engineering, 42.7 (Jul. 7, 1995) pp. 637-646.
(Continued)

*Primary Examiner* — Jon Eric C Morales
(74) *Attorney, Agent, or Firm* — Onello & Mello, LLP

(57) ABSTRACT

Methods of generating a graphical representation of cardiac information on a display screen are provided. The method comprises: electronically creating or acquiring an anatomical model of the heart including multiple cardiac locations; electronically determining a data set of source information corresponding to cardiac activity at the multiple cardiac locations; electronically rendering the data set of source information in relation to the multiple cardiac locations on
(Continued)

the display screen. Systems and devices for providing a graphical representation of cardiac information are also provided.

22 Claims, 13 Drawing Sheets

Related U.S. Application Data

(60) Provisional application No. 61/970,027, filed on Mar. 25, 2014.

(51) Int. Cl.
| | |
|---|---|
| A61B 5/287 | (2021.01) |
| A61B 5/339 | (2021.01) |
| A61B 8/00 | (2006.01) |
| A61B 18/14 | (2006.01) |
| A61B 90/00 | (2016.01) |
| A61B 5/318 | (2021.01) |
| A61B 18/00 | (2006.01) |

(52) U.S. Cl.
CPC ............ *A61B 5/7425* (2013.01); *A61B 5/743* (2013.01); *A61B 8/12* (2013.01); *A61B 8/445* (2013.01); *A61B 8/4483* (2013.01); *A61B 18/1492* (2013.01); *A61B 90/37* (2016.02); *A61B 5/318* (2021.01); *A61B 2018/00148* (2013.01); *A61B 2018/00267* (2013.01); *A61B 2018/00357* (2013.01); *A61B 2018/00577* (2013.01); *A61B 2505/05* (2013.01); *A61B 2576/023* (2013.01)

(58) Field of Classification Search
CPC ...... A61B 2018/00577; A61B 2505/05; A61B 2576/023; A61B 5/287; A61B 5/318; A61B 5/339; A61B 5/6858; A61B 5/7425; A61B 5/743; A61B 8/12; A61B 8/445; A61B 8/4483; A61B 90/37; G16H 30/40

See application file for complete search history.

(56) References Cited

U.S. PATENT DOCUMENTS

| | | | |
|---|---|---|---|
| 5,041,973 A | 8/1991 | Lebron et al. |
| 5,156,151 A | 10/1992 | Imran |
| 5,293,868 A | 3/1994 | Nardella |
| 5,482,472 A | 1/1996 | Garoni et al. |
| 5,499,981 A | 3/1996 | Kordis |
| 5,555,883 A | 9/1996 | Avitall |
| 5,595,183 A | 1/1997 | Swanson et al. |
| 5,601,084 A | 2/1997 | Sheehan et al. |
| 5,647,367 A | 7/1997 | Lum et al. |
| 5,662,108 A | 9/1997 | Budd et al. |
| 5,722,402 A | 3/1998 | Swanson et al. |
| 5,722,416 A | 3/1998 | Swanson et al. |
| 5,740,808 A | 4/1998 | Panescu et al. |
| 5,749,833 A | 5/1998 | Hakki et al. |
| 5,759,158 A | 6/1998 | Swanson |
| 5,782,239 A | 7/1998 | Webster, Jr. |
| 5,795,298 A | 8/1998 | Vesley et al. |
| 5,795,299 A | 8/1998 | Eaton et al. |
| 5,820,568 A | 10/1998 | Willis |
| 5,830,144 A | 11/1998 | Vesely |
| 5,846,198 A | 12/1998 | Killmann |
| 5,876,336 A | 3/1999 | Swanson et al. |
| 5,928,228 A | 7/1999 | Kordis et al. |
| 5,944,022 A | 8/1999 | Nardella et al. |
| 5,968,040 A | 10/1999 | Swanson et al. |
| 6,014,590 A | 1/2000 | Whayne et al. |
| 6,024,703 A | 2/2000 | Zanelli et al. |
| 6,066,096 A | 5/2000 | Smith et al. |
| 6,086,532 A | 7/2000 | Panescu et al. |
| 6,107,699 A | 8/2000 | Swanson |
| 6,115,626 A | 9/2000 | Whayne et al. |
| 6,187,032 B1 | 2/2001 | Ohyu et al. |
| 6,188,928 B1 | 2/2001 | Noren et al. |
| 6,216,027 B1 | 4/2001 | Willis et al. |
| 6,216,043 B1 | 4/2001 | Swanson et al. |
| 6,240,307 B1 | 5/2001 | Beatty et al. |
| 6,301,496 B1 | 10/2001 | Reisfeld |
| 6,396,198 B1 | 5/2002 | Okimura et al. |
| 6,400,981 B1 | 6/2002 | Govari |
| 6,490,474 B1 | 12/2002 | Willis et al. |
| 6,514,249 B1 | 2/2003 | Maguire et al. |
| 6,556,695 B1 | 4/2003 | Packer et al. |
| 6,574,492 B1 | 6/2003 | Ben-Haim et al. |
| 6,640,119 B1 | 10/2003 | Budd et al. |
| 6,695,785 B2 | 2/2004 | Brisken et al. |
| 6,716,166 B2 | 4/2004 | Govari |
| 6,728,562 B2 | 4/2004 | Budd et al. |
| 6,772,004 B2 | 8/2004 | Rudy |
| 6,773,402 B2 | 8/2004 | Govari et al. |
| 6,824,515 B2 | 11/2004 | Suorsa et al. |
| 6,826,420 B1 | 11/2004 | Beatty et al. |
| 6,826,421 B1 | 11/2004 | Beatty et al. |
| 6,839,588 B1 | 1/2005 | Rudy |
| 6,895,267 B2 | 5/2005 | Panescu et al. |
| 6,939,309 B1 | 9/2005 | Beatty et al. |
| 6,950,689 B1 | 9/2005 | Willis et al. |
| 6,970,733 B2 | 11/2005 | Willis et al. |
| 6,978,168 B2 | 12/2005 | Beatty et al. |
| 6,990,370 B1 | 1/2006 | Beatty et al. |
| 7,187,964 B2 | 3/2007 | Khoury |
| 7,187,973 B2 | 3/2007 | Hauck |
| 7,258,674 B2 | 8/2007 | Hillstead et al. |
| 7,263,397 B2 | 8/2007 | Hauck et al. |
| 7,285,094 B2 | 10/2007 | Nohara et al. |
| 7,285,119 B2 | 10/2007 | Stewart et al. |
| 7,289,843 B2 | 10/2007 | Beatty et al. |
| 7,291,146 B2 | 11/2007 | Steinke et al. |
| 7,351,914 B2 | 4/2008 | Kaneto et al. |
| 7,479,141 B2 | 1/2009 | Kleen et al. |
| 7,505,810 B2 | 3/2009 | Harlev et al. |
| 7,536,218 B2 | 5/2009 | Govari et al. |
| 7,573,182 B2 | 8/2009 | Savage |
| 7,689,261 B2 | 3/2010 | Mohr et al. |
| 7,766,838 B2 | 8/2010 | Yagi et al. |
| 7,841,986 B2 | 11/2010 | He et al. |
| 7,918,793 B2 | 4/2011 | Altmann et al. |
| 7,953,475 B2 | 5/2011 | Harlev et al. |
| 8,103,327 B2 | 1/2012 | Harlev et al. |
| 8,147,486 B2 | 4/2012 | Honour et al. |
| 8,150,499 B2 | 4/2012 | Gelbart et al. |
| 8,175,680 B2 | 5/2012 | Panescu |
| 8,200,314 B2 | 6/2012 | Bladen et al. |
| 8,208,998 B2 | 6/2012 | Beatty et al. |
| 8,221,411 B2 | 7/2012 | Francischelli et al. |
| 8,233,972 B2 | 7/2012 | Zhang |
| 8,311,613 B2 | 11/2012 | Danehorn |
| 8,320,711 B2 | 11/2012 | Altmann et al. |
| 8,346,339 B2 | 1/2013 | Kordis et al. |
| 8,360,786 B2 | 1/2013 | Duryea |
| 8,364,234 B2 | 1/2013 | Kordis et al. |
| 8,412,307 B2 | 4/2013 | Willis et al. |
| 8,417,313 B2 | 4/2013 | Scharf et al. |
| 8,428,690 B2 | 4/2013 | Li et al. |
| 8,447,377 B2 | 5/2013 | Harlev et al. |
| 8,454,596 B2 | 6/2013 | Ma et al. |
| 8,465,433 B2 | 6/2013 | Zwirn |
| 8,478,388 B2 | 7/2013 | Nguyen et al. |
| 8,512,255 B2 | 8/2013 | Scharf et al. |
| 8,571,647 B2 | 10/2013 | Harlev et al. |
| 8,700,119 B2 | 4/2014 | Scharf et al. |
| 8,755,861 B2 | 6/2014 | Harlev et al. |
| 8,825,130 B2 | 9/2014 | Just et al. |
| 8,825,134 B2 | 9/2014 | Danehorn |
| 8,918,158 B2 | 12/2014 | Scharf et al. |
| 8,934,988 B2 | 1/2015 | Persson et al. |
| 8,948,837 B2 | 2/2015 | Harlev et al. |

(56) References Cited

U.S. PATENT DOCUMENTS

| | | |
|---|---|---|
| 8,968,299 B2 | 3/2015 | Kauphusman et al. |
| 8,979,839 B2 | 3/2015 | De La Rama et al. |
| 8,989,842 B2 | 3/2015 | Li et al. |
| 9,011,423 B2 | 4/2015 | Brewster et al. |
| 9,023,027 B2 | 5/2015 | Bar-Tal et al. |
| 9,026,196 B2 | 5/2015 | Curran et al. |
| 9,031,642 B2 | 5/2015 | Ghosh |
| 9,037,259 B2 | 5/2015 | Mathur |
| 9,044,245 B2 | 6/2015 | Condie et al. |
| 9,113,807 B2 | 8/2015 | Koyrakh et al. |
| 9,167,982 B2 | 10/2015 | Scharf et al. |
| 9,186,081 B2 | 11/2015 | Afonso et al. |
| 9,186,212 B2 | 11/2015 | Nabutovsky et al. |
| 9,192,318 B2 | 11/2015 | Scharf et al. |
| 9,220,432 B2 | 12/2015 | Bukhman |
| 9,241,687 B2 | 1/2016 | McGee |
| 9,351,789 B2 | 5/2016 | Novichenok et al. |
| D758,596 S | 6/2016 | Perryman et al. |
| 9,358,398 B2 | 6/2016 | Moffitt et al. |
| 9,380,953 B2 | 7/2016 | Houben et al. |
| 9,474,486 B2 | 10/2016 | Eliason et al. |
| 9,480,525 B2 | 11/2016 | Lopes et al. |
| 9,486,355 B2 | 11/2016 | Gustus et al. |
| 9,492,227 B2 | 11/2016 | Lopes et al. |
| 9,492,228 B2 | 11/2016 | Lopes et al. |
| 9,498,192 B2 | 11/2016 | Hashimshony et al. |
| 9,504,395 B2 | 11/2016 | Scharf et al. |
| 9,526,573 B2 | 12/2016 | Lopes et al. |
| 9,549,708 B2 | 1/2017 | Mercanzini et al. |
| 9,579,149 B2 | 2/2017 | Kelly et al. |
| D782,686 S | 3/2017 | Werneth et al. |
| 9,585,588 B2 | 3/2017 | Marecki et al. |
| 9,603,651 B2 | 3/2017 | Ghosh |
| 9,610,024 B2 | 4/2017 | Scharf et al. |
| 9,675,266 B2 | 6/2017 | Afonso et al. |
| 9,713,730 B2 | 7/2017 | Mathur et al. |
| 9,717,555 B2 | 8/2017 | Chan et al. |
| 9,717,559 B2 | 8/2017 | Ditter et al. |
| 9,730,602 B2 | 8/2017 | Harlev et al. |
| 9,757,044 B2 | 9/2017 | Scharf et al. |
| 9,827,039 B2 | 11/2017 | Dandler et al. |
| 9,901,303 B2 | 2/2018 | Olson |
| 9,913,589 B2 | 3/2018 | Scharf et al. |
| 9,968,268 B2 | 5/2018 | Scharf et al. |
| 10,004,459 B2 | 6/2018 | Werneth et al. |
| 10,028,706 B2 | 7/2018 | Brockway et al. |
| 10,082,395 B2 | 9/2018 | Koyrakh et al. |
| 10,201,311 B2 | 2/2019 | Chou et al. |
| 10,296,707 B2 | 5/2019 | Passerini et al. |
| 10,405,828 B2 | 9/2019 | Deladi et al. |
| 10,593,234 B2 | 3/2020 | Zhu et al. |
| 10,653,318 B2 | 5/2020 | Welsh et al. |
| 11,278,231 B2 * | 3/2022 | Scharf .................. A61B 5/743 |
| 2001/0007070 A1 | 7/2001 | Stewart et al. |
| 2002/0026118 A1 | 2/2002 | Govari |
| 2002/0045810 A1 | 4/2002 | Ben-Haim |
| 2002/0099292 A1 | 7/2002 | Brisken et al. |
| 2002/0128565 A1 | 9/2002 | Rudy |
| 2002/0165441 A1 | 11/2002 | Coleman et al. |
| 2003/0036696 A1 | 2/2003 | Willis et al. |
| 2003/0065271 A1 | 4/2003 | Khoury |
| 2003/0078494 A1 | 4/2003 | Panescu et al. |
| 2003/0120318 A1 | 6/2003 | Hauck |
| 2003/0153907 A1 | 8/2003 | Suorsa et al. |
| 2003/0158477 A1 | 8/2003 | Panescu |
| 2003/0163046 A1 | 8/2003 | Nohara et al. |
| 2003/0176799 A1 | 9/2003 | Beatty et al. |
| 2003/0231789 A1 | 12/2003 | Willis et al. |
| 2003/0236466 A1 | 12/2003 | Tarjan et al. |
| 2004/0039312 A1 | 2/2004 | Hillstead et al. |
| 2004/0082870 A1 | 4/2004 | Rudy et al. |
| 2004/0082948 A1 | 4/2004 | Stewart et al. |
| 2004/0113498 A1 | 6/2004 | Kroenke |
| 2004/0254437 A1 | 12/2004 | Hauck et al. |
| 2005/0059880 A1 | 3/2005 | Mathias et al. |
| 2005/0101874 A1 | 5/2005 | Beatty et al. |
| 2005/0113665 A1 | 5/2005 | Mohr et al. |
| 2005/0148836 A1 | 7/2005 | Kleen et al. |
| 2005/0203375 A1 | 9/2005 | Willis et al. |
| 2006/0052716 A1 | 3/2006 | Beatty et al. |
| 2006/0058663 A1 | 3/2006 | Willis et al. |
| 2006/0058676 A1 | 3/2006 | Yagi et al. |
| 2006/0058692 A1 | 3/2006 | Beatty et al. |
| 2006/0058693 A1 | 3/2006 | Beatty et al. |
| 2006/0084884 A1 | 4/2006 | Beatty et al. |
| 2006/0084970 A1 | 4/2006 | Beatty et al. |
| 2006/0084971 A1 | 4/2006 | Beatty et al. |
| 2006/0084972 A1 | 4/2006 | Beatty et al. |
| 2006/0116576 A1 | 6/2006 | McGee et al. |
| 2006/0244177 A1 | 11/2006 | Kaneto et al. |
| 2007/0016007 A1 | 1/2007 | Govari et al. |
| 2007/0055150 A1 | 3/2007 | Donaldson et al. |
| 2007/0060832 A1 | 3/2007 | Levin |
| 2007/0083194 A1 | 4/2007 | Kunis et al. |
| 2007/0106146 A1 | 5/2007 | Altmann et al. |
| 2007/0167722 A1 | 7/2007 | Bladen et al. |
| 2007/0232949 A1 | 10/2007 | Saksena |
| 2008/0009758 A1 | 1/2008 | Voth |
| 2008/0146937 A1 | 6/2008 | Lee et al. |
| 2008/0287777 A1 | 11/2008 | Li et al. |
| 2008/0319297 A1 | 12/2008 | Danehorn |
| 2009/0024086 A1 | 1/2009 | Zhang et al. |
| 2009/0076483 A1 | 3/2009 | Danehorn |
| 2009/0082691 A1 | 3/2009 | Denison et al. |
| 2009/0131930 A1 | 5/2009 | Gelbart et al. |
| 2009/0143651 A1 | 6/2009 | Kallback et al. |
| 2009/0148012 A1 | 6/2009 | Altmann et al. |
| 2009/0171274 A1 | 7/2009 | Harlev et al. |
| 2009/0264781 A1 | 10/2009 | Scharf et al. |
| 2010/0023004 A1 | 1/2010 | Francischelli et al. |
| 2010/0076426 A1 | 3/2010 | de la Rama et al. |
| 2010/0094279 A1 | 4/2010 | Kauphusman et al. |
| 2010/0168578 A1 | 7/2010 | Garson, Jr. et al. |
| 2010/0256627 A1 | 10/2010 | Ma et al. |
| 2010/0279263 A1 | 11/2010 | Duryea |
| 2010/0286551 A1 | 11/2010 | Harlev et al. |
| 2010/0298690 A1 | 11/2010 | Scharf et al. |
| 2011/0045130 A1 | 2/2011 | Edens et al. |
| 2011/0077526 A1 | 3/2011 | Zwirn |
| 2011/0092809 A1 | 4/2011 | Nguyen et al. |
| 2011/0118726 A1 | 5/2011 | De La Rama et al. |
| 2011/0125172 A1 | 5/2011 | Gelbart et al. |
| 2011/0144510 A1 | 6/2011 | Ryu et al. |
| 2011/0172658 A1 | 7/2011 | Gelbart et al. |
| 2011/0201951 A1 | 8/2011 | Zhang |
| 2011/0213231 A1 | 9/2011 | Hall et al. |
| 2011/0230775 A1 | 9/2011 | Barley et al. |
| 2011/0270237 A1 | 11/2011 | Werneth et al. |
| 2012/0078077 A1 | 3/2012 | Harlev et al. |
| 2012/0082969 A1 | 4/2012 | Schwartz et al. |
| 2012/0123296 A1 | 5/2012 | Hashimshony et al. |
| 2012/0136231 A1 | 5/2012 | Markel |
| 2012/0143298 A1 | 6/2012 | Just et al. |
| 2012/0165667 A1 | 6/2012 | Altmann et al. |
| 2012/0172702 A1 | 7/2012 | Koyrakh et al. |
| 2012/0172859 A1 | 7/2012 | Condie et al. |
| 2012/0184863 A1 | 7/2012 | Harlev et al. |
| 2012/0265054 A1 | 10/2012 | Olson |
| 2012/0271138 A1 | 10/2012 | Kordis et al. |
| 2012/0271139 A1 | 10/2012 | Kordis et al. |
| 2012/0277574 A1 | 11/2012 | Panescu |
| 2012/0302912 A1 | 11/2012 | Moffitt et al. |
| 2012/0310064 A1 | 12/2012 | McGee |
| 2013/0006238 A1 | 1/2013 | Ditter et al. |
| 2013/0085361 A1 | 4/2013 | Mercanzini et al. |
| 2013/0096432 A1 | 4/2013 | Hauck |
| 2013/0158537 A1 | 6/2013 | Deladi et al. |
| 2013/0165916 A1 | 6/2013 | Mathur |
| 2013/0172715 A1 | 7/2013 | Just et al. |
| 2013/0190587 A1 | 7/2013 | Lopes et al. |
| 2013/0197614 A1 | 8/2013 | Gustus et al. |
| 2013/0225983 A1 | 8/2013 | Willis et al. |
| 2013/0226017 A1 | 8/2013 | Scharf et al. |
| 2013/0241929 A1 | 9/2013 | Massarwa et al. |

(56) References Cited

U.S. PATENT DOCUMENTS

| | | |
|---|---|---|
| 2013/0245433 A1 | 9/2013 | Deladi et al. |
| 2013/0245621 A1 | 9/2013 | Persson et al. |
| 2013/0253298 A1 | 9/2013 | Harlev et al. |
| 2013/0267853 A1 | 10/2013 | Dausch et al. |
| 2013/0274582 A1 | 10/2013 | Afonso et al. |
| 2013/0282084 A1 | 10/2013 | Mathur et al. |
| 2013/0304062 A1 | 11/2013 | Chan et al. |
| 2013/0304065 A1 | 11/2013 | Lopes et al. |
| 2013/0310827 A1 | 11/2013 | Brewster et al. |
| 2013/0330701 A1 | 12/2013 | Rubinstein et al. |
| 2014/0024910 A1 | 1/2014 | Scharf et al. |
| 2014/0095105 A1 | 4/2014 | Koyrakh et al. |
| 2014/0121470 A1 | 5/2014 | Scharf et al. |
| 2014/0148677 A1 | 5/2014 | Liempde et al. |
| 2014/0180150 A1 | 6/2014 | Scharf et al. |
| 2014/0221803 A1 | 8/2014 | Bar-Tal et al. |
| 2014/0235988 A1 | 8/2014 | Ghosh |
| 2014/0249505 A1 | 9/2014 | Bukhman |
| 2014/0257069 A1 | 9/2014 | Eliason et al. |
| 2014/0257071 A1 | 9/2014 | Curran et al. |
| 2014/0275921 A1 | 9/2014 | Harlev et al. |
| 2014/0276733 A1 | 9/2014 | VanScoy et al. |
| 2014/0276746 A1 | 9/2014 | Nabutovsky et al. |
| 2014/0276789 A1 | 9/2014 | Dandler et al. |
| 2014/0358143 A1 | 12/2014 | Novichenok et al. |
| 2015/0038862 A1 | 2/2015 | Gijsbers et al. |
| 2015/0196217 A1 | 7/2015 | Harlev et al. |
| 2015/0196219 A1 | 7/2015 | Scharf et al. |
| 2015/0208938 A1 | 7/2015 | Houben et al. |
| 2015/0223757 A1 | 8/2015 | Werneth et al. |
| 2015/0223863 A1 | 8/2015 | Ghosh |
| 2015/0257732 A1 | 9/2015 | Ryan |
| 2015/0257825 A1 | 9/2015 | Kelly et al. |
| 2015/0294082 A1 | 10/2015 | Passerini et al. |
| 2015/0342491 A1 | 12/2015 | Marecki et al. |
| 2015/0366508 A1 | 12/2015 | Chou et al. |
| 2015/0374252 A1 | 12/2015 | de la Rama et al. |
| 2016/0007869 A1 | 1/2016 | Scharf et al. |
| 2016/0038051 A1 | 2/2016 | Scharf et al. |
| 2016/0051321 A1 | 2/2016 | Salahieh et al. |
| 2016/0100770 A1 | 4/2016 | Afonso et al. |
| 2016/0128771 A1 | 5/2016 | Ditter et al. |
| 2016/0128772 A1 | 5/2016 | Reinders et al. |
| 2016/0192902 A1 | 7/2016 | Werneth et al. |
| 2016/0256112 A1 | 9/2016 | Brockway et al. |
| 2017/0035486 A1 | 2/2017 | Lopes et al. |
| 2017/0065204 A1 | 3/2017 | Ludwin et al. |
| 2017/0100049 A1 | 4/2017 | Scharf et al. |
| 2017/0202469 A1 | 7/2017 | Scharf et al. |
| 2017/0258347 A1 | 9/2017 | Scharf et al. |
| 2017/0311833 A1 | 11/2017 | Afonso et al. |
| 2017/0319180 A1 | 11/2017 | Henneken et al. |
| 2018/0055374 A1 | 3/2018 | Scharf et al. |
| 2018/0146948 A1 | 5/2018 | Chou et al. |
| 2018/0296114 A1 | 10/2018 | Welsh et al. |
| 2018/0315347 A1 | 11/2018 | Zhu et al. |
| 2019/0159729 A1 | 5/2019 | Chou et al. |
| 2020/0138317 A1 | 5/2020 | Scharf et al. |
| 2020/0187801 A1 | 6/2020 | Scharf et al. |
| 2021/0068694 A1 | 3/2021 | Chou et al. |

FOREIGN PATENT DOCUMENTS

| | | |
|---|---|---|
| CN | 1856213 | 11/2006 |
| CN | 101048100 | 10/2007 |
| CN | 201223445 | 4/2009 |
| CN | 201275144 | 7/2009 |
| CN | 102770085 | 11/2012 |
| CN | 104462650 | 3/2015 |
| EP | 1166714 | 1/2002 |
| EP | 1415608 | 10/2004 |
| EP | 1760661 | 3/2007 |
| EP | 1779787 | 5/2007 |
| EP | 2051625 | 4/2009 |
| EP | 2252203 | 11/2010 |
| EP | 2683293 | 1/2014 |
| EP | 2953550 | 8/2016 |
| JP | 08501477 | 2/1996 |
| JP | 08504333 | 5/1996 |
| JP | 08164140 | 6/1996 |
| JP | 10137207 | 5/1998 |
| JP | 11504541 | 4/1999 |
| JP | 2000510030 | 8/2000 |
| JP | 2000510250 | 8/2000 |
| JP | 2000358299 | 12/2000 |
| JP | 2001070269 | 3/2001 |
| JP | 2001522288 | 11/2001 |
| JP | 2002051998 | 2/2002 |
| JP | 2002113004 | 4/2002 |
| JP | 2002522106 | 7/2002 |
| JP | 2003509145 | 3/2003 |
| JP | 2003511098 | 3/2003 |
| JP | 2004350702 | 12/2004 |
| JP | 2005536313 | 12/2005 |
| JP | 2006511296 | 4/2006 |
| JP | 2006525072 | 11/2006 |
| JP | 2008149132 | 7/2008 |
| JP | 2009135109 | 6/2009 |
| JP | 2009136679 | 6/2009 |
| JP | 2011504363 | 2/2011 |
| JP | 2011507656 | 3/2011 |
| JP | 2012509701 | 4/2012 |
| JP | 2013188476 | 9/2013 |
| JP | 2014506171 | 3/2014 |
| JP | 2014514031 | 6/2014 |
| JP | 2014516723 | 7/2014 |
| JP | 2016511026 | 4/2016 |
| JP | 2017514553 | 6/2017 |
| WO | 9406349 | 3/1994 |
| WO | 9905971 | 2/1999 |
| WO | 0007501 | 2/2000 |
| WO | 0040166 | 7/2000 |
| WO | 0245608 | 6/2002 |
| WO | 03026722 | 4/2003 |
| WO | 2004026134 | 4/2004 |
| WO | 2006060613 | 6/2006 |
| WO | 2008014629 | 2/2008 |
| WO | 2009065042 | 5/2009 |
| WO | 2009090547 | 7/2009 |
| WO | 2011136867 | 11/2011 |
| WO | 2012068471 | 5/2012 |
| WO | 2012092016 | 7/2012 |
| WO | 2012100184 | 7/2012 |
| WO | 2012100185 | 7/2012 |
| WO | 2012110942 | 8/2012 |
| WO | 2012122517 | 9/2012 |
| WO | 2014124231 | 2/2013 |
| WO | 2013101257 | 7/2013 |
| WO | 2013123549 | 8/2013 |
| WO | 2014036439 | 3/2014 |
| WO | 20014059308 | 4/2014 |
| WO | 2014130169 | 8/2014 |
| WO | 2014137897 | 9/2014 |
| WO | 2015038607 | 3/2015 |
| WO | 2015148470 | 10/2015 |
| WO | 2016183179 | 11/2016 |
| WO | 2016183285 | 11/2016 |
| WO | 2016183468 | 11/2016 |
| WO | 2017192769 | 11/2017 |
| WO | 2017192775 | 11/2017 |
| WO | 2019144103 | 7/2019 |
| WO | 2019217430 | 11/2019 |
| WO | 2020097438 | 5/2020 |

OTHER PUBLICATIONS

Jackson, JD, "Surface Distributions of Charges and Dipoles and Discontinuities in the Electric Field and Potential", Classical Electrodynamics, 3rd edition, Dec. 1998, pp. 31-34.

Leif et al., "Geometric modeling based on polygonal meshes". Eurographics 2000 Tutorial, Aug. 21, 2000.

Partial European Search Report dated Apr. 29, 2014 issued in corresponding European Application No. 13176658.

(56) References Cited

OTHER PUBLICATIONS

Pullan et al. "The inverse problem of electrocardiology" Northeastern University Electrical and Computer Engineering, Feb. 23, 2007.
Stevenson et al. "Recording Techniques for Clinical Electrophysiology", Journal of Cardiovascular Electrophysiology, vol. 16, No. 9, Sep. 2005, pp. 1017-1022.
Van Oosterom A: "Solidifying the solid angle." 2002 Journal of Electrocardiology 2002 vol. 35 Suppl pp. 181-192 ISSN: 0022-0736.
Wolfgang Nolting: Elektrodynamik—Grundkurs Theoretische Physik 3, Springer Spectrum, p. 89-91.
Extended European Search Report dated Oct. 18, 2017 issued in European Application No. 15768711.
Extended European Search Report dated Oct. 4, 2018 issued in corresponding European Application No. 16793503.0.
Extended European Search Report dated Sep. 29, 2014 issued in corresponding European Application No. 13176658.
International Search Report and Written Opinion dated Apr. 8, 2019, issued in corresponding International Application No. PCT/US19/14498.
International Search Report and Written Opinion dated Aug. 11, 2016 issued in corresponding International Application No. PCT/US2016/032017.
International Search Report and Written Opinion dated Aug. 18, 2016 issued in corresponding International Application No. PCT/US16/32420.
International Search Report and Written Opinion dated Aug. 4, 2017 issued in corresponding International Application No. PCT/US17/30915.
International Search Report and Written Opinion dated Aug. 8, 2016 issued in corresponding European Application No. PCT/US2016/031823.
International Search Report and Written Opinion dated Dec. 12, 2017 issued in corresponding International Application No. PCT/US2017/056064.
International Search Report and Written Opinion dated Jan. 14, 2020 issued in International Application No. PCT/US2019/060433.
International Search Report and Written Opinion dated Jul. 21, 2020 issued in corresponding International Application No. PCT/US2020/028779.
International Search Report and Written Opinion dated Jul. 23, 2019 issued in corresponding International Application No. PCT/US2019/031131.
International Search Report and Written Opinion dated Jun. 26, 2015 issued in International Application No. PCT/US2015/022187.
International Search Report and Written Opinion dated Jun. 5, 2014 issued in corresponding International Application No. PCT/US2013/057579.
International Search Report and Written Opinion dated Mar. 10, 2015 issued in corresponding International Application No. PCT/US14/54942.
International Search Report and Written Opinion dated Mar. 5, 2013 issued in corresponding International Application No. PCT/US2012/028593.
International Search Report and Written Opinion dated May 20, 2014 issued in corresponding International Application No. PCT/US14/15261.
International Search Report and Written Opinion dated Sep. 14, 2020 issued in corresponding International Application No. PCT/US2020/036110.
International Search Report and Written Opinion dated Sep. 25, 2017, issued in corresponding Application No. PCT/US17/30922.
International Search Report dated Oct. 7, 2009 issued in corresponding International Application No. PCT/IB2009/000071.
International Search Report dated Apr. 21, 2008 in related International Application No. PCT/CH2007/000380.
Invitation to Pay Additional Fees issued on Jan. 8, 2014 in corresponding International Application No. PCT/US2013/057579.
Japanese Notice of Allowance dated Feb. 27, 2018 issued in corresponding Japanese Application No. 2015-530101.
Japanese Notice of Allowance dated Jul. 11, 2017 issued in corresponding Japanese Application No. 2013-557-926, with English language summary.
Japanese Notice of Allowance dated Jul. 7, 2020 issued in corresponding Japanese Application No. 2016558799, with English translation of allowed claims.
Japanese Notice of Allowance dated Jun. 11, 2019 issued in corresponding Japanese Application No. 2018-024907, with English translation.
Japanese Notice of Allowance dated Mar. 5, 2019 issued in corresponding Japanese Application No. 2018061040, with English translation.
Japanese Notice of Allowance dated Sep. 1, 2020 issued in corresponding Japanese Application No. 2017-559320, with English summary.
Japanese Notice of Allowance dated Sep. 18, 2018 issued in corresponding Japanese Application No. 2015-557091, with English language translation.
Japanese Office Action dated Aug. 28, 2018 issued in corresponding Japanese Application No. 2016-542062, with machine translation to English.
Japanese Office Action dated Dec. 11, 2018 issued in corresponding Japanese Application No. 2018-024907, with machine translation to English.
Japanese Office Action dated Feb. 16, 2016 issued in corresponding Japanese Application No. 2013-557-926, with English language summary.
Japanese Office Action dated Feb. 19, 2019 issued in corresponding Japanese Application No. 2016-558799, with machine translation to English.
Japanese Office Action dated Jan. 31, 2017 issued in corresponding Japanese Application No. 2013-557-926, with English language summary.
Japanese Office Action dated Jan. 7, 2020 issued in corresponding Japanese Application No. 2016-558799, with machine translation to English.
Japanese Office Action dated Jul. 23, 2019 issued in corresponding Japanese Application No. 2016-542062, with machine translation to English.
Japanese Office Action dated Jul. 28, 2020 issued in corresponding Japanese Application No. 2018-195960, with machine translation to English.
Japanese Office Action dated Jun. 27, 2017 issued in corresponding Japanese Application No. 2015-530101. with English language translation.
Japanese Office Action dated Jun. 29, 2021 issued in corresponding Japanese Application No. 2020-081074, with machine translation to English.
Japanese Office Action dated Jun. 30, 2020 issued in corresponding Japanese Application No. 2017559317, with machine translation to English.
Japanese Office Action dated Mar. 10, 2020 issued in corresponding Japanese Application No. 2017-559320, with machine translation to English.
Japanese Office Action dated Mar. 17, 2020 issued in corresponding Japanese Application No. 2019-071004, with machine translation to English.
Japanese Office Action dated Nov. 2, 2021 issued in corresponding Japanese Application No. 2020-192741, with English translation.
Japanese Office Action dated Oct. 10, 2017 issued in corresponding Japanese Application No. 2015-557091, with machine translation to English.
Japanese Office Action dated Oct. 15, 2019 issued in corresponding Japanese Application No. 2018-195960, with machine translation to English.
Japanese Office Action dated Sep. 26, 2017 issued in corresponding Japanese Application No. 2017-155346, with English translation.
Summons To Attend Oral Proceedings dated Dec. 20, 2019 issued in corresponding European Application No. 13763151.1.
Della Bella et al. "Non-contact mapping to guide catheter ablation of untolerated ventrical tachycardia" European Heart Journal, May 2002, 23(9)742-752.

(56) References Cited

OTHER PUBLICATIONS

Flavia et al. "Wave Similarity Mapping Shows the Spatiotemporal Distribution of Fibrillatory Wave Complexity in the Human Right Atrium During Paroxysmal and Chronic Atrial Fibrillation", Journal of Cardiovascular Electrophysiology, vol. 16, No. 10 (Oct. 2005) pp. 1071-1076.
Gupta et al. "Point of View Cardiac Mapping: Utility or Futility?", Indian Pacing and Electrophysiology Journal, vol. 2, No. 1, 2002, pp. 20-32.
Anatomy Warehouse, "Axis Heart Model", 2014, pp. 1-3, at http://www.anatomywarehouse.com/axis-scientific-2-part-deluxe-life-size-human-heart-a-104269. (Year: 2014).
Christoph Scharf et al. Declaration under 37 C.F.R. 1.132, Nov. 15, 2012.
Australian Examination Report dated Feb. 8, 2019 issued in corresponding Australian Application No. 2018250516.
Australian Examination Report dated Jun. 28, 2018 issued in corresponding Australian Patent Application No. 2014318872.
Australian Office Action dated Dec. 22, 2019 issued in corresponding Australian Application No. 2018278959.
Australian Office Action dated Feb. 26, 2018 issued in Australian Application No. 2017201560.
Australian Office Action dated Jan. 15, 2020 issued in corresponding Australian Application No. 2016262547.
Australian Office Action dated Jan. 26, 2019 issued in corresponding Australian Application No. 2018211348.
Australian Office Action dated Jul. 6, 2017 issued in corresponding Australian Application No. 2014214756.
Australian Office Action dated Jun. 14, 2018 issued in Australian Application No. 2014214756.
Australian Office Action dated Jun. 27, 2017 issued in corresponding Australian Application No. 2013308531.
Australian Office Action dated Mar. 16, 2020 issued in corresponding Australian Application No. 2016260522.
Australian Office Action dated Mar. 17, 2018 issued in corresponding Australian Application No. 2013308531.
Australian Office Action dated May 30, 2016 issued in related Australian Application No. 2012225250.
Australian Office Action dated Sep. 21, 2016 issued in corresponding Australian Application No. 2012225250.
Canadian Office Action dated Apr. 26, 2017 issued in corresponding Canadian Application No. 2932956.
Canadian Office Action dated Apr. 27, 2016 issued in corresponding Canadian Application No. 2747859.
Canadian Office Action dated Dec. 22 2015 issued in corresponding Canadian Application No. 2656898.
Canadian Office Action dated Jan. 22, 2018 issued in corresponding Canadian Application No. 2932956.
Canadian Office Action dated Jul. 12, 2019 issued in corresponding Canadian Application No. 2881457.
Canadian Office Action dated Mar. 30, 2017 issued in corresponding Canadian Application No. 2747859.
Canadian Office Action dated May 20, 2020 issued in corresponding Canadian Application No. 2881457.
Canadian Office Action dated Nov. 27, 2017 issued in corresponding Canadian Application No. 2829626.
Canadian Office Action dated Nov. 7, 2018 issued in corresponding Canadian Application No. 2932956.
Canadian Office Action dated Oct. 29, 2018 issued in corresponding Canadian Application No. 2829626.
Canadian Office Action dated Oct. 4, 2013 issued in corresponding Canadian Application No. 2659898.
Chinese Office Action dated Apr. 17, 2017 issued in corresponding Chinese Application No. 201480018328.4.
Chinese Office Action dated Apr. 8, 2020 issued in corresponding Chinese Application No. 201810153436.2.
Chinese Office Action dated Sep. 8, 2021 issued in corresponding Chinese Application No. 201680040709.1.
Communication Under Rule 71(3) EPC dated Nov. 15, 2021 issued in corresponding European Application No. 15768711.2.
Decision dated Jan. 16, 2018 issued for European Patent Application No. 09702094.5.
Decision dated Jan. 18, 2018 issued for European Patent Application No. 13176658.6.
European Office Action dated Apr. 23, 2018 issued in corresponding European Application No. 07785075.8.
European Office Action dated Apr. 28, 2014 issued in corresponding European Application No. 09702094.5.
European Office Action dated Feb. 29, 2016 issued in corresponding European Application No. 07785075.8.
European Office Action dated Feb. 6, 2019 issued in corresponding European Application No. 14843283.4.
European Office Action dated Jan. 28, 2019 issued in corresponding European Application No. 14748567.6.
European Office Action dated Jan. 31, 2018 issued in corresponding European Application No. 13763151.1.
Office Action dated Jun. 15, 2020 issued in corresponding European Application No. 15768711.2.
European Office Action dated Mar. 21, 2017 issued in corresponding European Application No. 07785075.8.
European Office Action dated Mar. 9, 2016 issued in corresponding European Application No. 09702094.5.
European Office Action dated Mar. 9, 2016 issued in corresponding European Application No. 13176658.6.
European Office Action dated Nov. 7, 2017 issued in corresponding European Application No. 15768711.
Extended European Search Report dated Aug. 10, 2021 issued in corresponding European Application No. 19741310.7.
Extended European Search Report dated Dec. 13, 2021 issued in corresponding European Application No. 19800090.3.
Extended European Search Report dated Dec. 5, 2018 issued in corresponding European Application No. 16793622.8.
Extended European Search Report dated Jul. 23, 2021 issued in corresponding European Application No. 21150862.7.
Extended European Search Report dated Jul. 8, 2016 issued in corresponding European Application No. 14748567.6.
Extended European Search Report dated Mar. 14, 2017 issued in corresponding European Application No. 14843283.4.
Extended European Search Report dated Nov. 26, 2019 issued in corresponding European Application No. 19184148.5.

\* cited by examiner

CARDIAC ANALYSIS USER INTERFACE SYSTEM AND METHOD

CROSS REFERENCES TO RELATED APPLICATIONS

The present application is a continuation application of U.S. patent application Ser. No. 15/128,563, entitled "Cardiac Analysis User Interface System and Method", filed on Sep. 23, 2016, United States Publication Number US-2017-0202469, published Jul. 20, 2017, which is a U.S. National Stage entry of International Patent Application No.: PCT/US2015/022187, filed Mar. 24, 2015, which claims priority under 35 USC 119(e) to U.S. Provisional Application Ser. No. 61/970,027, entitled CARDIAC ANALYSIS USER INTERFACE SYSTEM AND METHOD, filed Mar. 25, 2014, which is incorporated herein by reference in its entirety.

The present application, while not claiming priority to, may be related to Applicant's US Design Patent Application No. 29/475,273, entitled Transducer-Electrode Arrangement, filed Dec. 2, 2013, the entirety of which is incorporated herein by reference.

The present application, while not claiming priority to, may be related to Applicant's co-pending U.S. patent application Ser. No. 14/422,941, entitled Catheter System and Methods of Medical Uses of Same, Including Diagnostic and Treatment Uses for the Heart, filed Feb. 5, 2015, and International Application No. PCT/US2013/057579, entitled Catheter System and Methods of Medical Uses of Same, Including Diagnostic and Treatment Uses for the Heart, filed Aug. 30, 2013, which claimed priority to U.S. Provisional Patent Application No. 61/695,535, entitled System and Method for Diagnosing and Treating Heart Tissue, filed Aug. 31, 2012, each of which is hereby incorporated by reference.

The present application, while not claiming priority to, may be related to Applicant's co-pending U.S. patent application Ser. No. 14/003,671, entitled Device and Method For the Geometric Determination of Electrical Dipole Densities on the Cardiac Wall, filed Mar. 9, 2012, and International Application No. PCT/US2012/028593, entitled Device and Method for the Geometric Determination of Electrical Dipole Densities on the Cardiac Wall, filed Mar. 9, 2012, which claimed priority to U.S. Provisional Patent Application No. 61/451,357, entitled Device and Method for the Geometric Determination of Electrical Dipole Densities on the Cardiac Wall, filed Mar. 10, 2011, each of which is hereby incorporated by reference.

The present application, while not claiming priority to, may be related to U.S. patent application Ser. No. 13/946,712, entitled A Device and Method for the Geometric Determination of Electrical Dipole Densities on the Cardiac Wall, filed Jul. 19, 2013, which is a continuation of U.S. Pat. No. 8,512,255, entitled A Device and Method for the Geometric Determination of Electrical Dipole Densities on the Cardiac Wall, filed Jul. 16, 2010, published as US20100298690, which was a 35 USC 371 a national stage application of Patent Cooperation Treaty Application No. PCT/IB09/00071 filed Jan. 16, 2009, entitled A Device and Method for the Geometric Determination of Electrical Dipole Densities on the Cardiac Wall, published as WO 2009/090547, which claimed priority to Swiss Patent Application 00068/08 filed Jan. 17, 2008, each of which is hereby incorporated by reference.

The present application, while not claiming priority to, may be related to U.S. patent application Ser. No. 14/547,258, entitled Method and Device for Determining and Presenting Surface Charge and Dipole Densities on Cardiac Walls, filed Nov. 14, 2014, which is a continuation of U.S. patent application Ser. No. 13/858,715, entitled Method and Device for Determining and Presenting Surface Charge and Dipole Densities on Cardiac Walls, filed Apr. 8, 2013, which is a continuation of U.S. Pat. No. 8,417,313, entitled Method and Device for Determining and Presenting Surface Charge and Dipole Densities on Cardiac Walls, filed Feb. 3, 2009, published as US2009264781, which was a 35 USC 371 national stage filing of PCT Application No. CH2007/000380, entitled Method and Device for Determining and Presenting Surface Charge and Dipole Densities on Cardiac Walls, filed Aug. 3, 2007, published as WO 2008/014629, which claimed priority to Swiss Patent Application No. 1251/06 filed Aug. 3, 2006, each of which is hereby incorporated by reference.

FIELD OF INTEREST

The invention relates to the field of systems and methods for analyzing cardiac activity and for diagnosing and treating cardiac related abnormalities, and in particular to systems and methods that display cardiac-related information useful in such activities.

BACKGROUND

For identifying the origin(s) of cardiac arrhythmias it is common practice to measure the electric potentials located on the inner surface of the heart with electroanatomic mapping systems. For example, for this purpose electrode catheters can be inserted into the heart and moved around while recording cardiac potentials during normal heart rhythm or cardiac arrhythmia. If the arrhythmia has a regular activation sequence, the timing of local activation measured from the cardiac potentials at each site visited by the electrode can be combined across many sites and over many heart beats during the arrhythmia, to create a three dimensional "Local Activation Time" (LAT) map of the electric activation. By doing this, information on the location of the source of arrhythmia(s) and mechanisms, i.e., foci and reentry circuits, can be diagnosed to initiate or guide treatment (e.g., radiofrequency ablation).

This mapping procedure is often aided by computer systems generating three dimensional maps of catheter positions by localizing the catheter with the help of magnetic fields (the so called Carto System) or transthoracic impedances (by Localisa and NavX). Because all the points of such maps are obtained by electrode positions in contact with the cardiac surface, this mapping system is called "conventional contact mapping". It has the inherent limitation that cardiac activation can only be assessed simultaneously at the points in contact with the myocardium. Hence, an instantaneous map of the entire cardiac activation is impossible because the entire heart chamber cannot be contacted simultaneously without compromising blood circulation. Instantaneous mapping of the entire electric activation of the heart chamber, however, might be advantageous in unstable arrhythmias of short duration, for which the conventional mapping procedures (moving the electrode around during the arrhythmia) are too time-consuming compared to this short duration and are therefore unable to capture a clinically relevant electric activation map. In addition, an instantaneous map of cardiac electric activation might be advantageous during irregular arrhythmias or arrhythmias with non-constant activation sequences that render accumulation of activation times from contact mapping impossible. Finally, instantaneous maps of cardiac activation are probably also faster and easier obtained, than a contact map generated by time consuming catheter movements to different areas of the heart in all sorts of cardiac arrhythmias.

The disadvantage of contact mapping can be overcome by "non-contact mapping," which allows for mapping cardiac activation of a heart chamber simultaneously without contact to the cardiac wall. For this purpose, for instance, a multi electrode array mounted on an inflatable balloon can be inserted into the heart. The geometry of the heart chamber is obtained either (i) by reconstruction of a contact map, which is obtained from an accumulation of 3D surface positions during movements with an electrode catheter within the heart chamber, or (ii) by importing imaging data from computed tomography or MRI (magnetic resonance imaging).

Once the geometry of the cardiac chamber is outlined in a map the information of a simultaneous recording of cardiac far field potentials (unipoles) by the multi electrode array can be extrapolated to the desired cardiac map using advanced mathematical methods. This non-contact mapping has the advantage that it provides the entire electric activation measured by far field unipolar potentials either in sinus rhythm or during arrhythmia without the need for moving an electrode catheter around the cardiac chamber. This information allows for a single beat analysis of cardiac activation and, therefore, unstable, irregular or multifocal arrhythmias can be tracked and treated. However, the disadvantage of non-contact mapping is that it relies on far field potentials, which do not allow for the same precision in localization as contact mapping (i.e. measuring local electrograms (potentials) of cardiac activation by touching the endocardium at the site of interest with a mapping electrode).

Furthermore, non-contact mapping is more prone to artifact generation and interference from potentials generated by cardiac re-polarization and adjacent heart chambers (atria/ventricles). These drawbacks can be overcome to a certain extent with several filtering techniques. However, in many cases these drawbacks also render the localization of cardiac arrhythmias a time-consuming and frustrating intervention.

Therefore, the advantages of non-contact mapping, i.e. the instantaneous cardiac activation maps, have to be balanced against the disadvantages, i.e. the decreased spatial resolution due to recording of far field signals, filtering of artifacts, etc.

Another method for the non-invasive localization of cardiac arrhythmias is body surface mapping. In this technique multiple electrodes are attached to the entire surface of the thorax and the information of the cardiac electrical activation is simultaneously measured from the body surface potentials, called the electrocardiogram (ECG), which are assimilated omtp LAT maps. Complex mathematical methods are required in order to determine the local time of electric activation in a heart model, for instance, one obtained from CT or MRI imaging giving information on cardiac size and orientation within the thoracic cavity.

The disadvantage of both mapping methods, i.e. contact and non-contact types, is the representation of the electric activity of the heart by means of potentials, which are the result of a summation of ionic charge-sources within the membrane of all cardiac cells spanning the entire 3D volume of the cardiac tissue. This summation of electric forces generated by the ionic charge-sources in cardiac cells provides for the potentials that are measured by current mapping systems.

Research has indicated that the use of the surface charge densities (i.e. their distribution) or dipole densities (i.e. their distribution) to generate a distribution map (or maps), if successfully, practicably, and reliably determined, can lead to more detailed and precise information on electric ionic activity of local cardiac cells than the conventional determination made using potentials (or voltages). Surface charge density or dipole densities represent a precise and sharp set of information of the electric activity with good spatial resolution, whereas potentials resulting from a summation of charge densities provide only a diffuse picture of electric activity. The electric nature of cardiac cell membranes comprising ionic charges of proteins and soluble ions can be precisely described by surface charge and dipole densities, but not by conventional measures of potential. The surface charge densities and/or dipole densities cannot be directly measured in the heart, but instead must be mathematically and accurately calculated starting from measured potentials. In other words, the information of voltage maps obtained by conventional mapping systems can be greatly refined when calculating surface charge densities or dipole densities from these. However, determining surface and dipole densities from voltage information and maps is not a trivial mathematical exercise. U.S. Pat. No. 8,417,313 B2 and U.S. Pat. No. 8,512,255 B2, each to Scharf et al., describe approach for determining surface and dipole densities from voltage information and maps.

Surface charge density means surface charge (Coulombs) per unit area ($cm^2$). A dipole, as such, is a neutral element, wherein one part comprises a positive charge and the other part comprises the same, but negative charge. A dipole or surface charge map could be considered to represent the electric nature of cellular membranes better than voltage maps, because in a biological environment, ion charges are not macroscopically separated.

Currently, mapping systems display cardiac images and activity based on measured potentials, not dipole or surface charge densities. As discussed above, this inherently includes inaccuracies, since voltages are averaged and/or smoothed field data and dipole or surface charge densities are much more accurate source data. Additionally, such display systems do not provide a real-time or near real-time display of the heart or cardiac activity because the volume of rapidly changing cardiac-generated voltage data tends to be far too large for real-time or near real-time mapping using such systems. In fact, such mapping and display systems represent an image of the heart that is not accurate, such as due to left atrial enlargement that can occur during mapping and treatment procedures. A displayed image of the heart cannot be rapidly and accurately updated using current systems, so the practitioner must work with the inaccurate cardiac image. This is particularly troublesome, for example, when the practitioner is attempting to precisely locate heart tissue for ablation—which requires some amount of guesswork by the practitioner using conventional imaging and display systems.

SUMMARY

Methods of generating a graphical representation of cardiac information on a display screen are provided. The method comprises: electronically creating or acquiring an anatomical model of the heart including multiple cardiac locations; electronically determining a data set of source information corresponding to cardiac activity at the multiple cardiac locations; electronically rendering the data set of source information in relation to the multiple cardiac locations on the display screen. Systems and devices for providing a graphical representation of cardiac information are also provided.

In accordance with one aspect of the present disclosure, provided is a method of generating a graphical representation of cardiac information on a display screen. The method comprises: electronically creating an anatomical model of the heart including multiple cardiac locations; electronically determining a data set of source information corresponding to cardiac activity at the multiple cardiac locations; and electronically rendering the data set of source information in relation to the multiple cardiac locations on the display screen.

In various embodiments, the source information can be data representing, at a location in 3D space, a physical property or properties discrete to the specific location in 3D space.

In various embodiments, the source information can comprise recording signals from at least one sensor.

In various embodiments, the at least one sensor can comprise multiple sensors.

In various embodiments, the multiple sensors can be mounted to an expandable array constructed and arranged for placement within a cardiac chamber.

In various embodiments, the at least one sensor can comprise: electrode; pH sensor; temperature sensor; or combinations of two or more thereof.

In various embodiments, the source information can comprise: dipole density information; surface charge density information; pH information; temperature information; or combinations of two or more thereof.

In various embodiments, electronically determining a data set of source information can comprise electronically determining multiple sequential data sets of source information representing different phases of at least one cardiac cycle.

In various embodiments, the at least one cardiac cycle can comprise multiple cardiac cycles.

In various embodiments, the multiple sequential data sets can represent dynamic data sets that are updated at least thirty times per second.

In various embodiments, the multiple sequential data sets can represent or include dynamic data sets that are updated at least once per second.

In various embodiments, the multiple sequential data sets can represent or include dynamic data sets that are updated at least once every 30 minutes.

In various embodiments, the source information can be presented in the form of or using a differentiating map.

In various embodiments, the differentiating map can comprise a color map.

In various embodiments, the differentiating map can comprise a map of value differentiating parameters including: color; contrast; brightness; hue; saturation level; or combinations of two or more thereof.

In various embodiments, the method can comprise electronically rendering the anatomical model of the heart on the display screen.

In various embodiments, the anatomical model can be created using signals from at least one ultrasound transducer.

In various embodiments, the method can comprise displaying a static image of the heart on the display screen.

In various embodiments, the static image can comprise an image of the heart temporally proximate the end of systole.

In various embodiments, the static image can comprise an image of the heart temporally proximate the end of diastole.

In various embodiments, the static image of the heart can be updated at least once every thirty minutes.

In various embodiments, the method can comprise displaying a dynamic image of the heart comprising multiple images of a cardiac cycle on the display screen.

In various embodiments, the method can comprise displaying a dynamic image of the heart comprising multiple images of multiple cardiac cycles on the display screen.

In various embodiments, the method can comprise updating the multiple images of a cardiac cycle at least once every thirty minutes.

In various embodiments, the method can comprise rendering a data set of field information on the display screen.

In various embodiments, the data set of field information can comprise a data set of voltage information.

In various embodiments, the data set of field information can correspond to the multiple cardiac locations and can be optionally associated with the multiple cardiac locations on the display screen.

In various embodiments, the method can comprise displaying the data set of field information in a side-by-side arrangement with the data set of source information.

In various embodiments, the method can comprise displaying the data set of field information in an overlay arrangement with the data set of source information.

In various embodiments, the method can comprise displaying the data set of field information in an alternating arrangement with the data set of source information.

In various embodiments, the method can comprise producing calculated information and electronically rendering the calculated information on the display screen.

In various embodiments, the calculated information can be electronically rendered on the display screen in relation to one or more cardiac locations.

In various embodiments, the calculated information can comprise information based on recordings from at least one ultrasound transducer.

In various embodiments, the calculated information can comprise information based on recordings from an array of ultrasound transducers positioned in a cardiac chamber.

In various embodiments, the calculated information can comprise: cardiac chamber volume; cardiac wall thickness; average cardiac wall thickness; a cardiac chamber dimension; ejection fraction; cardiac output; cardiac flow rate; cardiac contractility; cardiac wall motion; or combinations of two or more thereof.

In various embodiments, the calculated information can comprise information based on recordings from at least one electrode.

In various embodiments, the calculated information can comprise information based on recordings from an array of electrodes positioned in a cardiac chamber.

In various embodiments, the calculated information can comprise: voltage at a heart surface location; dipole state at a heart surface location; or combinations of two or more thereof.

In various embodiments, the calculated information can comprise quantitative information.

In various embodiments, the calculated information can be rendered on the display in a form including: numerals; bar chart; pie chart; or combinations of two or more thereof.

In various embodiments, the calculated information can comprise mathematically processed recorded information.

In various embodiments, the recorded information can comprise information recorded by a component including: one or more electrodes; one or more ultrasound transducers; one or more sensors; or combinations of two or more thereof.

In various embodiments, the mathematical processing can comprise processing including: summing; averaging; integrating; differentiating; finding the mean; finding a maximum; finding a minimum; or combinations of two or more thereof.

In various embodiments, the recorded information can comprise information recorded by one or more electrodes.

In various embodiments, the calculated information can comprise information including: dipole density information; surface charge density information; or combinations of two or more thereof.

In various embodiments, the calculated information can comprise mathematically processed dipole density or surface charge density information.

In various embodiments, the mathematical processing can comprise processing including: summing; averaging; integrating; differentiating; finding the mean; finding a maximum; finding a minimum; or combinations of two or more thereof.

In various embodiments, the recorded information can comprise information recorded by one or more ultrasound transducers.

In various embodiments, the calculated information can represent a measure of heart contractility, and wherein the calculated information is rendered on the display screen.

In various embodiments, the method can comprise identifying an undesired contractility decrease based on the calculated information.

In various embodiments, the calculated information can represent a measure of heart enlargement, and wherein the calculated information is rendered on the display screen.

In various embodiments, the calculated information can represent a measure of left atrial enlargement.

In various embodiments, the method can comprise identifying an undesired heart enlargement based on the calculated information.

In various embodiments, the calculated information can comprise a measurement of a change in patient information over a time period.

In various embodiments, the calculated information can comprise a comparison of patient information to a threshold.

In various embodiments, the method can comprise changing the appearance of the calculated information on the display screen when the threshold is exceeded.

In various embodiments, changing the appearance can comprise changing a parameter including: color; boldness; font; size; static or dynamic presentation, or combinations of two or more thereof.

In various embodiments, the method can comprise activating an alert when the threshold is exceeded.

In various embodiments, the method can comprise electronically rendering additional patient information on the display screen.

In various embodiments, the additional patient information can comprise information including: age; sex; race; height; weight; patient ID; or combinations of two or more thereof.

In various embodiments, the additional patient information can comprise information including: blood pressure; heart rate; cardiac cycle length; pulse oximetry; respiration rate; or combinations of two or more thereof.

In various embodiments, the additional patient information can comprise quantitative information.

In various embodiments, the method can comprise representing the quantitative information on the display screen by a graphic element including: numerals; bar chart; pie chart; graph; plot; or combinations of two or more thereof.

In various embodiments, the method can comprise performing a therapeutic procedure on the patient based on at least the determined source information.

In various embodiments, the therapeutic procedure can be performed based on the rendered source information.

In various embodiments, the therapeutic procedure can comprise a cardiac ablation procedure.

In various embodiments, the cardiac ablation procedure can comprise ablating at least tissue of the left atrium.

In various embodiments, display of the data set of source information in relation to the multiple cardiac locations can be a user interactive display.

In various embodiments, user interactive display can be responsive to a user input to: pause, initiate, and/or record dynamic display of cardiac activity; store, display, or output a data value associated with at least one cardiac location; display or output an associated information in a secondary window or frame providing graphical, numerical, or textual information relating to cardiac activity represented by the data set; zoom in on, zoom out from, and/or rotate a cardiac image; isolate a portion of the cardiac image; reveal a cross-section or slice through the cardiac image; or combinations of two or more thereof.

In various embodiments, associated information can include an ECG, EKG, or both.

In accordance with various aspects of the present invention, provided is a system configured and arranged to provide a graphical representation of cardiac information on a display screen. The system comprises: a first receiver configured to receive cardiac geometry information and to create an anatomical model of the heart including multiple cardiac locations; a second receiver configured to receive information including: source information; field information; or combinations of two or more thereof, and to determine a set of source information corresponding to cardiac activity at the multiple cardiac locations; and a display screen configured to provide the data set of source information in relation to the multiple cardiac locations.

In various embodiments, the source information can be data representing, at a location in 3D space, a physical property or properties discrete to the specific location in 3D space.

In various embodiments, the source information can include dipole density data determined for a point on the surface of the heart.

In various embodiments, the source information can comprise: dipole density information; surface charge density information; pH information; temperature information; or combinations of two or more thereof.

In various embodiments, the system can comprise at least one ultrasound transducer configured to provide the cardiac geometry information to the first receiver.

In various embodiments, the at least one ultrasound transducer can comprise multiple ultrasound transducers.

In various embodiments, the multiple ultrasound transducers can be constructed and arranged in an expandable array.

In various embodiments, the system can comprise at least one sensor configured to provide the information received by the second receiver.

In various embodiments, the at least one sensor can comprise an electrode.

In various embodiments, the at least one sensor can comprise: pH sensor; temperature sensor; or combinations of two or more thereof.

In various embodiments, the system can comprise an imaging device configured to provide the cardiac geometry information to the first receiver.

In various embodiments, the imaging device can comprise: a Computed Tomography apparatus; an MRI apparatus; an Ultrasound apparatus; a multi-electrode mapping catheter; a multi-transducer imaging catheter such as an imaging catheter comprising an array of ultrasound transducers; or combinations of two or more thereof.

In various embodiments, the system display of the data set of source information in relation to the multiple cardiac locations can be a user interactive display.

In various embodiments, the system user interactive display can be responsive to a user input to: pause, initiate, and/or record dynamic display of cardiac activity; store, display, or output a data value associated with at least one cardiac location; display or output an associated information in a secondary window or frame providing graphical, numerical, or textual information relating to cardiac activity represented by the data set; zoom in on, zoom out from, and/or rotate a cardiac image; isolate a portion of the cardiac image; reveal a cross-section or slice through the cardiac image; or combinations of two or more thereof.

In various embodiments, the system associated information can include an ECG, EKG, or both.

In various embodiments, the system can comprise a therapeutic device configured to treat the patient based on the source information provided on the display.

In various embodiments, the therapeutic device can be an ablation catheter.

In accordance with aspects of the present invention, provided is a cardiac information display method as shown and described in reference to the figures herein.

In accordance with aspects of the present invention, provided is a cardiac information display system as shown and described in reference to the figures herein.

BRIEF DESCRIPTION OF THE DRAWINGS

The present invention will become more apparent in view of the attached drawings and accompanying detailed description. The embodiments depicted therein are provided by way of example, not by way of limitation, wherein like reference numerals refer to the same or similar elements. The drawings are not necessarily to scale, emphasis instead being placed upon illustrating aspects of the invention. In the drawings.

DETAILED DESCRIPTION OF PREFERRED EMBODIMENTS

Figure 1:
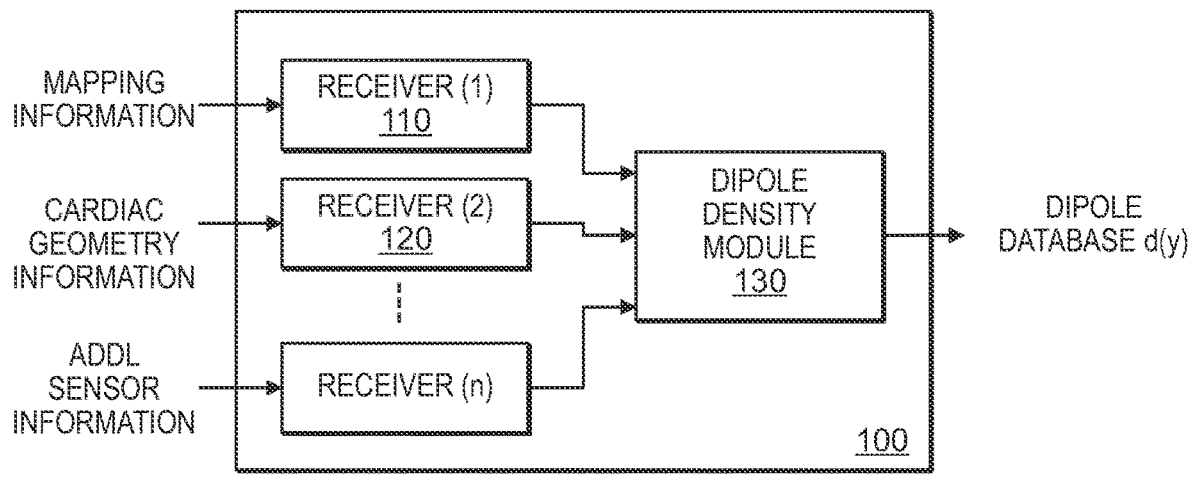
FIG. 1 illustrates a block diagram of an embodiment of a device for determining a database table of dipole densities d(y) and/or surface charge densities ρ(P',t) of at least one heart chamber, in accordance with aspects of the present invention.

Various exemplary embodiments will be described more fully hereinafter with reference to the accompanying drawings, in which some exemplary embodiments are shown. The present inventive concept may, however, be embodied in many different forms and should not be construed as limited to the exemplary embodiments set forth herein.

It will be understood that, although the terms first, second, etc. are be used herein to describe various elements, these elements should not be limited by these terms. These terms are used to distinguish one element from another, but not to imply a required sequence of elements. For example, a first element can be termed a second element, and, similarly, a second element can be termed a first element, without departing from the scope of the present invention. As used herein, the term "and/or" includes any and all combinations of one or more of the associated listed items.

It will be understood that when an element is referred to as being "on" or "connected" or "coupled" to another element, it can be directly on or connected or coupled to the other element or intervening elements can be present. In contrast, when an element is referred to as being "directly on" or "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, steps, operations, elements, and/or components, but do not preclude the presence or addition of one or more other features, steps, operations, elements, components, and/or groups thereof.

Spatially relative terms, such as "beneath," "below," "lower," "above," "upper" and the like may be used to describe an element and/or feature's relationship to another element(s) and/or feature(s) as, for example, illustrated in the figures. It will be understood that the spatially relative terms are intended to encompass different orientations of the device in use and/or operation in addition to the orientation depicted in the figures. For example, if the device in the figures is turned over, elements described as "below" and/or "beneath" other elements or features would then be oriented "above" the other elements or features. The device may be otherwise oriented (e.g., rotated 90 degrees or at other orientations) and the spatially relative descriptors used herein interpreted accordingly.

To the extent that functional features, operations, and/or steps are described herein, or otherwise understood to be included within various embodiments of the inventive concept, such functional features, operations, and/or steps can be embodied in functional blocks, units, modules, operations and/or methods. And to the extent that such functional blocks, units, modules, operations and/or methods include computer program code, such computer program code can be stored in a computer readable medium, e.g., such as non-transitory memory and media, that is executable by at least one computer processor.

As used herein, the terms "subject" and "patient" refer to any animal, such as a mammal like livestock, pets, and preferably a human. Specific examples of "subjects" and "patients" include, but are not limited to, individuals requiring medical assistance, diagnosis, and/or treatment, for example, patients with an arrhythmia, such as atrial fibrillation (AF).

Surface charge density means surface charge (Coulombs) per unit area ($cm^2$). A dipole, as such, is a neutral element, wherein one part comprises a positive charge and the other part comprises the same, but negative charge. A dipole or surface charge map could be considered to represent an electric nature of cellular membranes better than voltage maps, because in a biological environment, ion charges are not macroscopically separated.

The terms "map" and "mapping" can include "electrical map", "electrical mapping", "anatomical map", "anatomical mapping", "device map" and "device mapping", each of which is defined herein below.

The terms "electrical map" and "electrical mapping" can include recording, processing and/or displaying electrical information, such as electrical information recorded by one or more electrodes of the present invention. This electrical information includes, but is not limited to: cardiac or other tissue voltage measurements; cardiac or other tissue bipolar and/or unipolar electrograms; cardiac or other tissue surface charge data; cardiac or other tissue dipole density data; cardiac or other tissue monophasic action potentials; and combinations of these.

The terms "anatomical map" and "anatomical mapping" can include recording, processing and/or displaying anatomical information, such as anatomical information provided by one or more ultrasound transducers of the present invention and/or one or more electrodes of the present invention. This anatomical information includes, but is not limited to: two or three dimensional representations of tissue such as one or more chambers of a heart; tissue wall thicknesses such as the thickness of an atrial or ventricular wall; distance between two tissue surfaces; and combinations of these. In some embodiments, a dipole density map is provided by using information provided by multiple electrodes and multiple ultrasound transducers, such as is described in U.S. Pat. No. 8,512,255 B2.

The terms "device map" and "device mapping" can include recording, processing and/or displaying of device distance information, such as information comprising the distance between a device or device component and another object, such as tissue or another device or device component.

The term "patient information" can include physiologic and other information related to the patient, including but not limited to source information and field information, as defined herein, that relates to the patient's heart or other patient location. Patient information can include information which is derived from or is otherwise based on recordings made by one or more sensors, such as one or more electrodes, ultrasound transducers and/or other sensors of the present invention. Patient information can include mathematically processed patient information, such as patient information that is averaged, summed, integrated, differentiated and/or otherwise mathematically processed to create new patient information. Patient information can include patient demographic information, including but not limited to: age; sex; race; height; weight; and patient ID (e.g. an ID assigned to the patient by a hospital).

The term "cardiac information" can include patient physiologic and other information related to the patient's heart, including but not limited to source information and field information, as defined herein, that relates to the patient's heart and/or cardiac activity.

The systems and device of the present invention include one or more sensors or transducers, such as electrodes and ultrasound transducers. In various embodiments, any pair of electrodes can be constructed and arranged to provide distance information, such as the distance between that pair of electrodes, or the distance between one of the electrodes and one or more proximate components (e.g., a component at a known distance from one or both of the electrodes in the pair). By delivering and recording an electric signal between electrodes of known separation distances, the signal can by processed and/or calibrated according to one or more known separation distances (e.g., the separation distance between two electrodes fixedly mounted to a rigid structure at a pre-determined distance). Calibrated signal values can be combined across adjacent sets of electrode pairs to accurately estimate the distance between any pair (e.g. any arbitrary pair of electrodes on any one or more devices of the system) of electrodes for which the separation distance is not known. Known and calculated separation distances can be used as "reference" electrodes and combined to triangulate the unknown position of one or more "marker" electrodes, such as an electrode positioned on the present invention or on a separate or external device and positioned proximate the present invention. The process of triangulation can be used to dynamically localize the multi-dimensional position of any or all of the electrodes either individually and/or as a combined entity in multi-dimensional space. Numerous distance measurement techniques can be used.

Further, any or all electrodes can be used to deliver electric energy, such as radiofrequency energy.

FIGS. 1-12 illustrate embodiments of devices, systems and methods that can be used for determining dipole (or surface charge) densities from the cardiac activity of a patient or subject. However, the present invention is not limited to these particular configurations. The description will generally refer to "dipole densities," which should be interpreted to include, either additionally or alternatively, surface charge densities, unless otherwise stated, understood by those skilled in the art.

Referring now to FIG. 1, a block diagram of an embodiment of a dipole and/or surface charge density system including device 100 configured to determine a database table of dipole and/or surface charge densities of at least one heart chamber of a patient is illustrated.

Device 100 can include a plurality of receivers, e.g., receivers (1), (2) . . . (n), configured to receive one or more types of information from a patient, associated system, and/or other sensors. In this embodiment, device 100 includes a first receiver 110 configured to receive electrical potentials from a separate device, such as a device including a multi-electrode mapping catheter (e.g., placed in the circulating blood within a chamber of the patient's heart). Device 100 can further include a second receiver 120 configured to receive cardiac geometry information (e.g., the geometric contour of the cardiac chamber wall), such as from an instrument including, but not limited to: Computed Tomography; MRI; Ultrasound; a multi-electrode mapping catheter; a multi-transducer imaging catheter such as an imaging catheter comprising an array of ultrasound transducers; and combinations of these. In some embodiments, first receiver 110 receives information from an array of electrodes placed in a chamber of the heart, and second receiver 120 receives information from an array of ultrasound transducers also placed in a chamber of the heart. In these embodiments, the electrodes and ultrasound transducers can be included on a single deployable basket or other expandable assembly, such as is described herebelow in reference to FIG. 5A or 5C. Alternatively or additionally, a standard geometry can be loaded representing a model of the heart, such as a model including the geometry of the cardiac chamber. In some embodiments, a receiver, e.g., receiver (n), can be provided to enable device 100 to receive information from electrodes or other types of sensors that collect "source information," e.g., temperature or pH sensors. As used herein, "source information" is data representing, at a location in 3D space, a physical property or properties discrete to the specific location in 3D space. As contrasted to "field information," which, as used herein, is data representing, at a location in 3D space, a physical property or properties of a continuum extending through the 3D space.

Device 100 further includes a dipole density module 130 which comprises mathematical processing elements, such as a computer or other electronic module including software and/or hardware for performing mathematical or other calculations when executed by at least one computer processor. Dipole density module 130 receives electrical mapping information and/or other information (hereinafter "mapping information") from first receiver 110 and cardiac geometry information from second receiver 120. Dipole density module 130 preferably uses one or more algorithms to correlate and/or otherwise process the received mapping and geometry information, such as to produce a database table of dipole and/or surface charge densities (e.g. comprising multiple sequential data sets that represent one or more phases of one or more cardiac cycles). In some embodiments, the dipole and/or surface charge density information (or other source information) is updated at least once per second. In other embodiments, the dipole density information (or other source information) is updated as least once per 10 seconds. Accordingly, dipole density module 130 can be configured to produce a database or database table of dipole densities, surface charge densities, or both.

In some embodiments, the geometrical model of the cardiac chamber is processed by dipole density module 130 into multiple small polygons, such as multiple small triangles or other polygons (e.g., trapezoids, squares, rectangles, pentagons, hexagons, octagons, and so forth), hereinafter, collectively referred to as "triangles." When the triangles or other polygons are sufficiently small, the dipole and/or surface charge density at each triangle can be regarded as constant. In a preferred embodiment, a standard cardiac chamber of 4-6 cm diameter is divided up into over 1000 triangles. In another preferred embodiment, the number of triangles determined by dipole density module 130 is based on the size of the heart chamber. With the electrodes positioned in a cardiac chamber by a clinician, such as an electrophysiologist, the potentials at each electrode are recorded. Each triangle is seen by the corresponding electrode under a certain solid angle.

As used herein, the term "solid angle" is the angle subtended by a triangle on the heart wall at a position x of observation. When viewed from location x, straight lines are drawn from point x to the boundaries of the triangle, and a sphere is constructed of radius r=1 with a center of x. The straight lines then define the spherical triangle on the surface of the sphere. The solid angle is proportional to the surface area of the projection of that object onto a sphere centered at the point x.

The dipole density module 130 computes the solid angle $\hat{\omega}(x,y)$ subtended by each triangle at position y on each electrode at position x on the multi-electrode catheter. If the dipole density at the triangle is d(y), the triangle contributes $\hat{\omega}(x,y)$ times d(y) to the potential V(x) at the position x on the multi-electrode catheter. The total measured potential V(x) is the sum resulting from all the triangles. A detailed description is provided in reference to FIG. 3 herein below.

In some embodiments, dipole density module 130 can implement a progressive algorithm that can be modified and/or refined in order to improve spatial and/or time resolution of the database of dipole densities that are produced. The dipole densities d(y) are obtained by solving a linear system of equations. This calculation requires some care to avoid numerical instabilities. Thereby a map of dipole and/or surface charge densities can be created at corresponding time intervals. The synthesis of the maps generates a cascade of the activation sequence of each corresponding heart beat (also referred to herein as "cardiac cycle") that can be used to define the origin of the electrical activity, arrhythmias and/or diagnose cardiac disease.

The measuring electrodes used can be placed in the blood flow in a heart chamber, a relatively homogeneous condition, such that the mathematical analysis is well applicable. In a preferred embodiment, skin electrodes are also implemented such that dipole density module 130 can use the information received from the skin electrodes to calculate and/or recalculate the dipole densities for the cardiac wall. The spatial resolution which can be obtained by invasive (i.e., placed in the chamber) multi-electrode potential measurements correlates to the number of electrodes that can be placed in any cardiac chamber, such as the Left Atrium (LA). Skin placed electrodes, such as electrodes placed on the thorax, are not space limited and can be used to enhance calculations of the dipole densities. Application of electrical information measured from skin electrodes at known locations on the torso can enhance the accuracy of dipole and/or surface charge density calculations by adding independent complementary information from the opposite side of the dipole layer, as compared to information obtained from an electrode located within the heart chamber.

Due mainly to the inhomogeneous structure of the body, it is difficult to localize the actual sources of the skin electrode measured potentials. A highly complicated boundary value problem must be solved with boundary conditions that are poorly known, and previous attempts at determining the "action potential" from body surface ECG (alone) have not been very successful. The badly defined boundary value problem can be avoided by an additional measurement (in addition to the skin electrode measurements) of the chamber-inserted multi-electrode array of the present invention. A small sinusoidal voltage $V_1$ is applied to each electrode l=1, ... L on the electrode array in the heart, and the resulting voltages $W_k$, k=1, ... K is measured at the surface electrodes. This yields the K×L transition matrix $A_{kl}$ $$W_k = \sum_{l=1}^{L} A_{kl} V_l. \qquad (1)$$

Calculating solid angles produces the linear transformation $B_{ln}$ between the electrode array potentials $V_1$ and the dipole densities $d_n$, n=1, ... N of N regions of the heart wall:

$$V_l = \sum_{n=1}^{N} B_{ln} d_n. \qquad (2)$$

N is chosen to be N=K+L where K is the number of surface electrodes and L is the number of internally placed array electrodes.

Substituting equation (2) into (1) we have:

$$W_k = \sum_{l=1}^{L} \sum_{n=1}^{N} A_{kl} B_{ln} d_n. \qquad (3)$$

Therefore, by simultaneous measuring of the potentials of the cardiac activity with all K+L electrodes, N=K+L dipole densities of N regions on the heart wall can be calculated. This method yields a higher spatial resolution than the L array electrodes alone. In the solution of the linear system of equations (2)+(3), regularization techniques must be used (e.g. Tikhonov regularization and its modifications) in order to avoid numerical instabilities.

In some embodiments, other types of information can be captured, such as a temperature from a temperature sensor (e.g. a thermocouple) or pH from a pH sensor. The associated sensor can be placed at multiple locations along a cardiac surface while data is recorded. Module 130 can be used to correlate the recordings provided by the sensor to the anatomical information.

Figure 2:
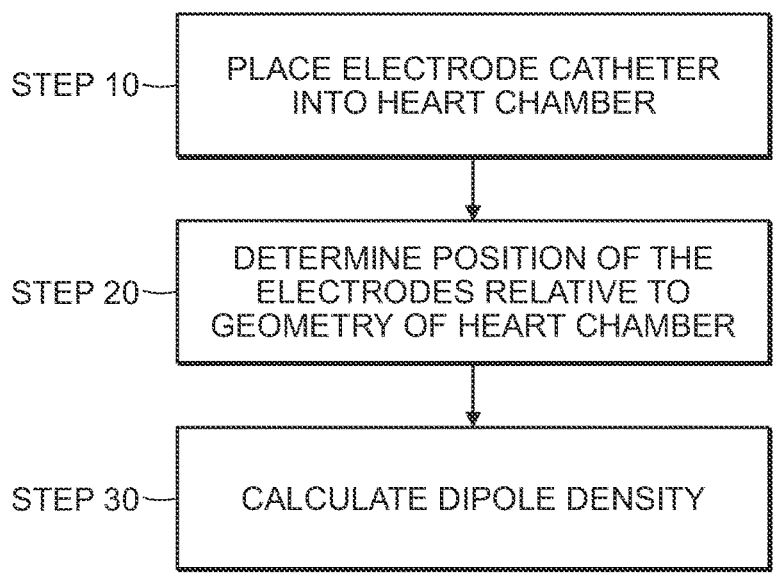
FIG. 2 illustrates a flow chart of an embodiment of a preferred method for determining a database table of dipole densities and/or surface charge densities ρ(P',t) of at least one heart chamber, in accordance with aspects of the present invention.

Referring now to FIG. 2, an embodiment of a preferred method for determining a database table of dipole (and/or surface charge) densities of at least one heart chamber of a patient is illustrated. In Step 10, a multi-electrode array catheter device is placed within the corresponding heart chamber. In Step 20, a model of the heart including geometry of the corresponding heart chamber is created (i.e. electronically created). In some embodiments, the model of the heart is created in relation to the multi-electrode array position. In some embodiments, the model of the heart comprises a static model comprising the geometry of one or more cardiac chambers representing that geometry at one particular reference point in a cardiac cycle (e.g. temporally proximate the end of systole or the end of diastole). The geometry of the static heart model can comprise a single image (e.g. created one time) or it can be updated over time (e.g. updated by capturing chamber geometry information at the same reference point in multiple sequential or non-sequential cardiac cycles). In some embodiments, the static heart model is updated at least once every thirty minutes. Alternatively or additionally, the model of the heart comprises a dynamic model (also referred to as a "beating heart model"). The dynamic model can comprise the cardiac geometry at multiple reference points of a single cardiac cycle (i.e. multiple images for a single heart beat) or it can be updated over time (e.g. by capturing sets of images at similar reference points in the cardiac cycle over multiple heart beats). In some embodiments, the dynamic heart model is updated at least 30 times per second (e.g. to provide a continuous image of the heart at 30 frames of video per second). In other embodiments, the dynamic heart model is updated at least once every 100 milliseconds, at least once every second, at least once every minute, or at least once every thirty minutes. In some embodiments, source information and/or field information is updated at least 30 times per second (e.g. to provide a continuous image of changing source information and/or field information at 30 frames of video per second). In other embodiments, source information and/or field information is updated at least once every 100 milliseconds, at least once every second, at least once every minute, or at least once every thirty minutes.

In some embodiments, the heart chamber geometry is provided by image-producing sensors (e.g. ultrasound sensors) from the same catheter device or a separate catheter device placed in the heart chamber. Alternatively or additionally, the model of the heart including heart chamber geometry is created (i.e. electronically created) from information provided by an imaging device external to the patient (e.g. a fluoroscope, computer tomography device, ultrasound imager, MRI) before and/or after the multi-electrode array of electrodes has been placed in the heart chamber. The surface of the geometry of the corresponding heart chamber model can be divided into small triangles, typically at least 1000 small triangles.

In Step 30, the dipole density d(y) can be calculated (i.e. electronically determined) from the measured potential values and the calculated solid angles. The measurements can be repeated successively during the cardiac cycle, such as to achieve sufficient resolution over time. The information of the time dependent dipole densities can be depicted as an activation map of the corresponding heart chamber for the given heartbeat. The information can be used to diagnose and/or treat a patient with a cardiac disease or disorder, such as atrial fibrillation or other cardiac arrhythmia. Alternatively or additionally, the surface charge density can be calculated in Step 30. In either or both cases, the dipole and/or surface charge densities can be stored in a database or database table, in Step 30.

In various embodiments, the information can be used to determine cardiac wall treatment locations for lesion creation to treat an arrhythmia, such as a lesion created in the Left or Right atrium, by an RF, microwave, laser, ultrasound and/or cryogenic ablation catheter. In some embodiments, the multiple electrode mapping array is placed in a ventricle and the dipole densities are determined for the ventricular wall, such as to detect ischemia or quantify myocardial function.

Figure 3:
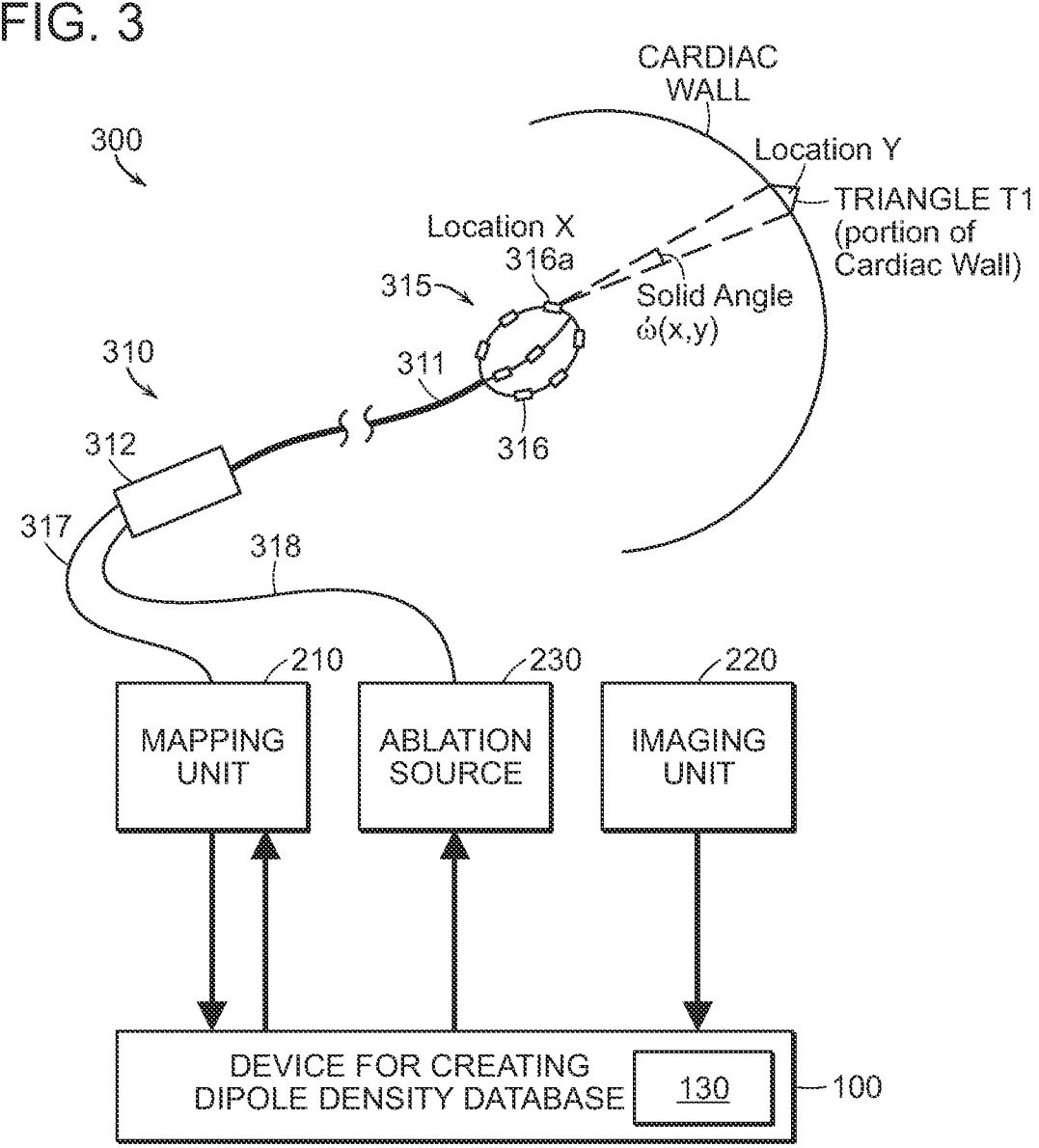
FIG. 3 illustrates a schematic view of an embodiment of a system for determining a database table of dipole densities and/or surface charge densities ρ(P',t) of at least one heart chamber with help of the solid angle ω(x,y), in accordance with aspects of the present invention.

Referring now to FIG. 3, an embodiment of a system for determining a database table of dipole densities and/or other information of at least one heart chamber of a patient is illustrated.

System 300 includes device 100, which can be configured to create a database (or table) of dipole densities d(y) based on electrical potential measurements within the heart chamber and image information relating to the heart chamber, as has been described herein above. Alternatively or additionally, device 100 can be configured to create a database of other information, such as other local information regarding surface charge densities, temperature and/or pH levels at a cardiac surface. System 300 further includes imaging unit 220, which is configured to provide a two or three-dimensional image of the heart chamber relative to information provided by device 100. Imaging unit 220 can perform at least one of fluoroscopy, Computed Tomography, MRI and/or ultrasound imaging, as examples of imaging technologies. Imaging unit 220 can produce any form of real or virtual models of the cardiac chambers, such that a mesh analysis (e.g. using triangles, polygons, etc.) is possible.

System 300 further includes mapping catheter 310, which includes shaft 311, shown inserted into a chamber of a patient's heart, such as the Left Atrium (LA). At the proximal end of shaft 311 is handle 312. At the distal end of shaft 311 is an array 315 including multiple electrodes 316 and/or multiple other sensors configured to record local information and/or field information. Array 315 is shown in a basket construction, but numerous other constructions can be used including multiple independent arms, spiral arrays, electrode, ultrasound sensor and/or other sensor-covered balloons, and other constructions configured to place multiple sensors and/or transducers into a two or three-dimensional arrangement. In a preferred embodiment, any catheter with a multi-dimensional array of electrodes or other sensors can be used to supply the mapping or other information to device 100. In various embodiments, alternatively or additionally, the electrodes and/or sensors can include sensors to sense other types of "source information," e.g., temperature and pH, as examples. Handle 312 can include one or more controls, not shown but such as one or more controls to steer shaft 311 and/or control one or more sensors or transducers of array 315, such as to activate one or more electrodes 316.

Figure 5A:
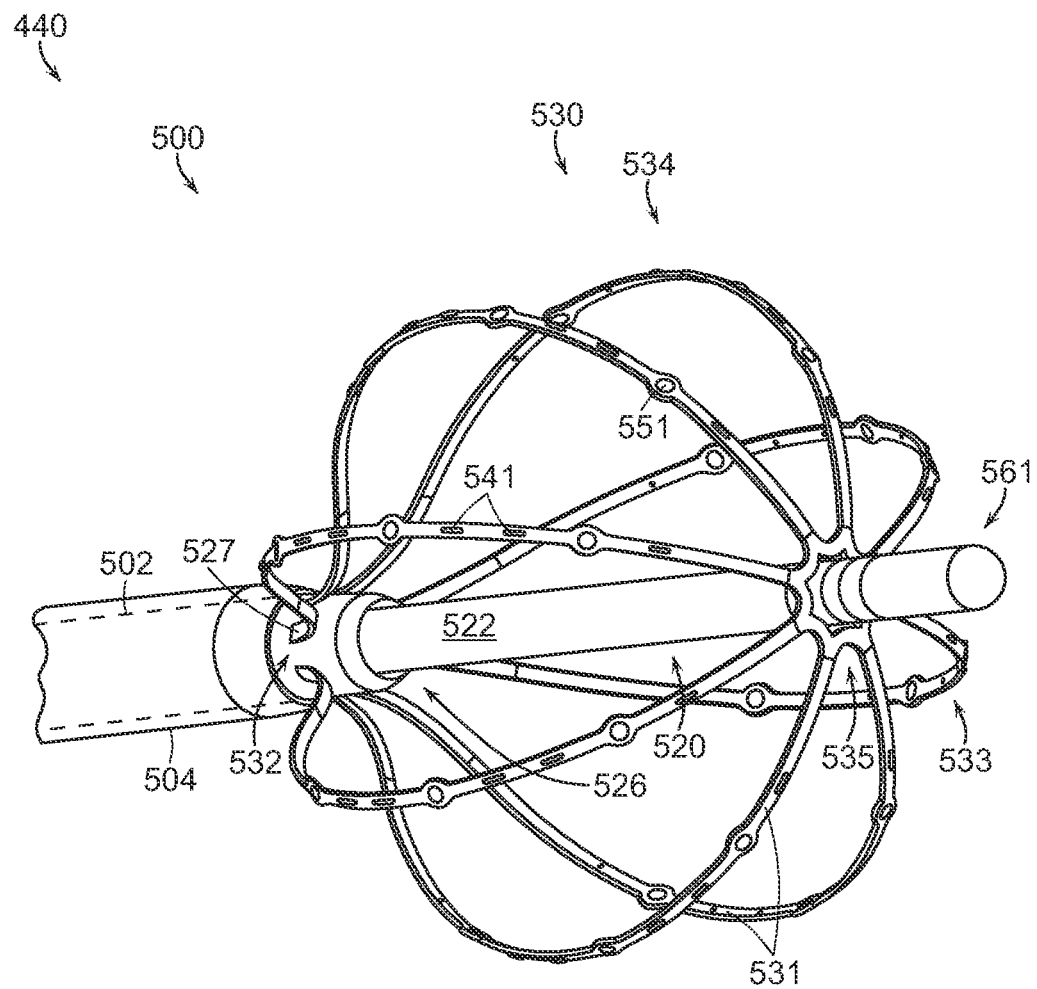
FIG. 5A is a perspective view of the distal portion of a system for treating a patient including an ablation catheter slidingly received by the shaft of a diagnostic catheter and FIG. 5B is a perspective view of the system of FIG. 5A, with the ablation catheter in a bent configuration for treating a patient, in accordance with aspects of the present invention.
Figure 5B:
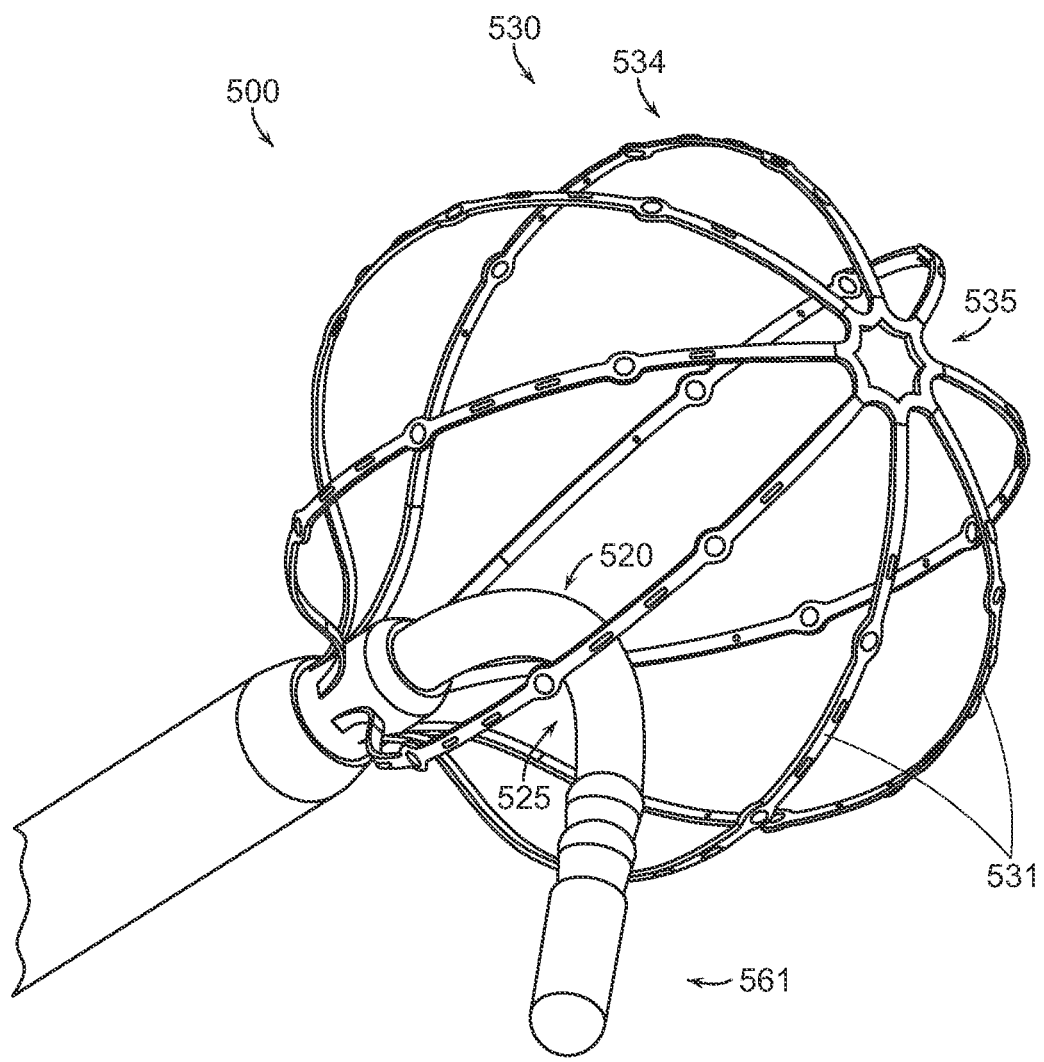
Figure 5C:
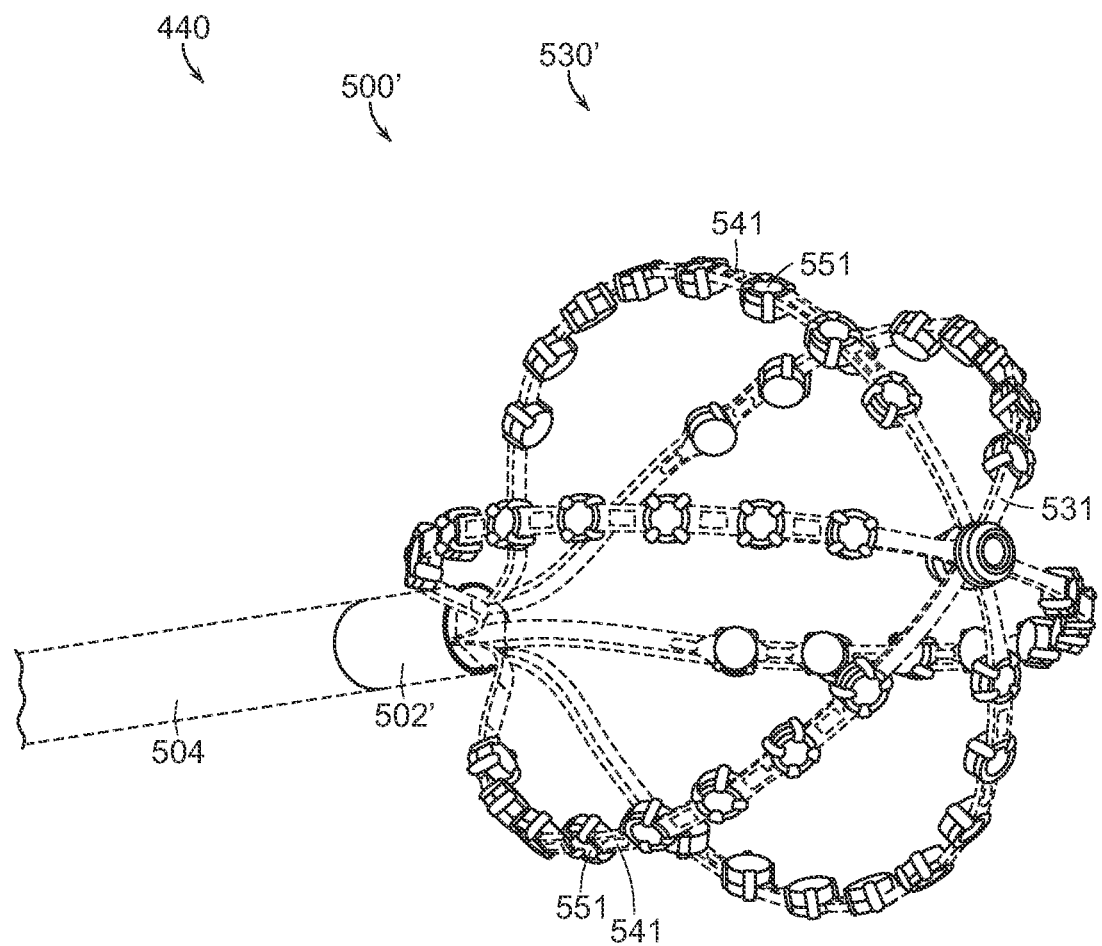
FIG. 5C is a perspective view of the distal portion of a system for determining a database of dipole and/or surface charge densities, in accordance with aspects of the present invention.

In some embodiments, catheter 310 can include one or more types of imaging transducers, such as ultra-sound transducers (USTs) built into catheter 310 or array 315, such as is described herebelow in reference to catheter 500 of FIG. 5A or catheter 500' of FIG. 5C. Such imaging transducers could be used to obtain imaging information to generate, maintain, update and/or augment the image of the heart, in conjunction with imaging unit 220.

Electrodes 316 are connected to wires, not shown, but traveling proximally, passing through handle 312 to cable 317, which is electrically connected to a mapping unit 210, such as an electrocardiogram (ECG) unit. Mapping unit 210 includes a monitor for displaying information, such as the potentials recorded by electrodes 316, as well as the dipole density or other information produced by device 100. In an alternative embodiment, device 100 further includes a monitor, not shown, but configured to display one or more of: dipole density information; surface charge information; potentials recorded by electrodes 316; information recorded by one or more sensors such as one or more temperature and/or pH sensors; and cardiac chamber contours and other geometry information. In a preferred embodiment, dipole density and/or recorded potentials information is shown in reference to a multi-dimensional representation of the heart chamber into which catheter 310 is inserted. In an alternative embodiment, imaging unit 220 can include a device configured to create an image of the cardiac chamber from signals recorded from an sensor array catheter, such as catheter 310 of FIG. 3, catheter 500 of FIG. 5A or catheter 500' of FIG. 5C.

System 300 can include a device for treating a cardiac arrhythmia, such as ablation source 230, which is electrically attached to electrodes 316 via cable 318. Alternatively or additionally, ablation source 230 can be operably attached (e.g. via wires, fluid delivery tubes and/or optical fibers) to a different ablation catheter, such as a single or multiple ablation element catheter configured to deliver ablation energy such as RF energy, microwave energy, laser energy, ultrasound energy, cryogenic energy, or other tissue disrupting energy.

As shown in FIG. 3, triangle T1, defined by device 100, is at location Y. Array 315 includes multiple electrodes 316, such as electrode 316a positioned at location X. The geometric relationship between triangle T1 and location X is defined by the solid angle, angle $\omega(X,Y)$. Device 100 includes dipole density module 130 such that each triangle at location y contributes $\omega(x,y)$ times the dipole density d(y) to the potential V(x) at the position x for each electrode of array 315. Solid angle $\omega(x,y)$, as defined above, corresponds to the triangle at a location y and the electrode at positions x on the multi-electrode array 315. The dipole density module 130 of device 100 determines from the total measured potential V(x), which is the sum resulting from all the triangles defined by device 100, the desired dipole density d(y).

When sufficient potential values V(x) are measured (e.g. from 10 to 10,000 with increasing number of measured potentials providing more accurate and/or spatially detailed results), the dipole density d(y) at many equally distributed regions y on the cardiac wall is calculated by solving a linear equation system. By interpolation of the measured potentials (e.g. with help of splines) their number of regions used in the calculation can be increased. The solid angle $\omega(x,y)$ of a region is the sum of the solid angles of the individual triangles in the region on the cardiac wall. This calculation of dipole density results, such as via an automatic computer program forming at least part of dipole density module 130.

In some embodiments, the results are presented in a visual, anatomical format, such as depicting the dipole densities on a geometric image of the cardiac wall in relation to time (t). This format allows a clinician, such as an electrophysiologist, to determine the activation sequence on the cardiac wall, such as to determine treatment locations for a cardiac arrhythmia. The results can be shown on a display of mapping unit 210, or on a separate unit such as a display included with device 100, display not shown but preferably a color monitor. In a preferred embodiment, the device of the present invention is implemented as, or includes, a software program that is executable by at least one processor. The software program can be integrated into one or more of: an ECG system; a cardiac tissue ablation system; an imaging system; a computer; and combinations of these.

In some embodiments, the multi-electrode catheter 310 includes at least 10 electrodes 316 and/or other sensor, configured to provide local information and/or field information in relation to a multi-dimensional representation of a heart. The electrodes 316 are preferably positioned in a spherical geometry, such as a spherical geometry created in a basket catheter. Elliptical electrode array geometries can be used, such as those provided in the Ensite Array Catheter, manufactured by St. Jude Medical of St. Paul Minnesota. In an alternative embodiment, multiple catheters are inserted into the heart chamber to provide the multiple electrodes.

In some embodiments, the electrodes 316 of the multi-electrode mapping array 315 are repositioned during the method of determining dipole densities. Repositioning of electrodes 316 and/or other sensors or transducers of array 315 can be beneficial to increase the number of measured potential values, if electrode 316 positions are known. Therefore, repositioning is in concordance with adjustment of the geometry map in relation to the multi-electrode mapping array 315.

In some embodiments, array 315 further comprises one or more transducers, such as one or more ultrasound transducers (USTs), as described variously herein. Also in some embodiments, either alternatively or in addition to the electrodes 316, array 315 can include non-electrode sensors, such as temperature sensors and/or pH sensors.

Figure 4:
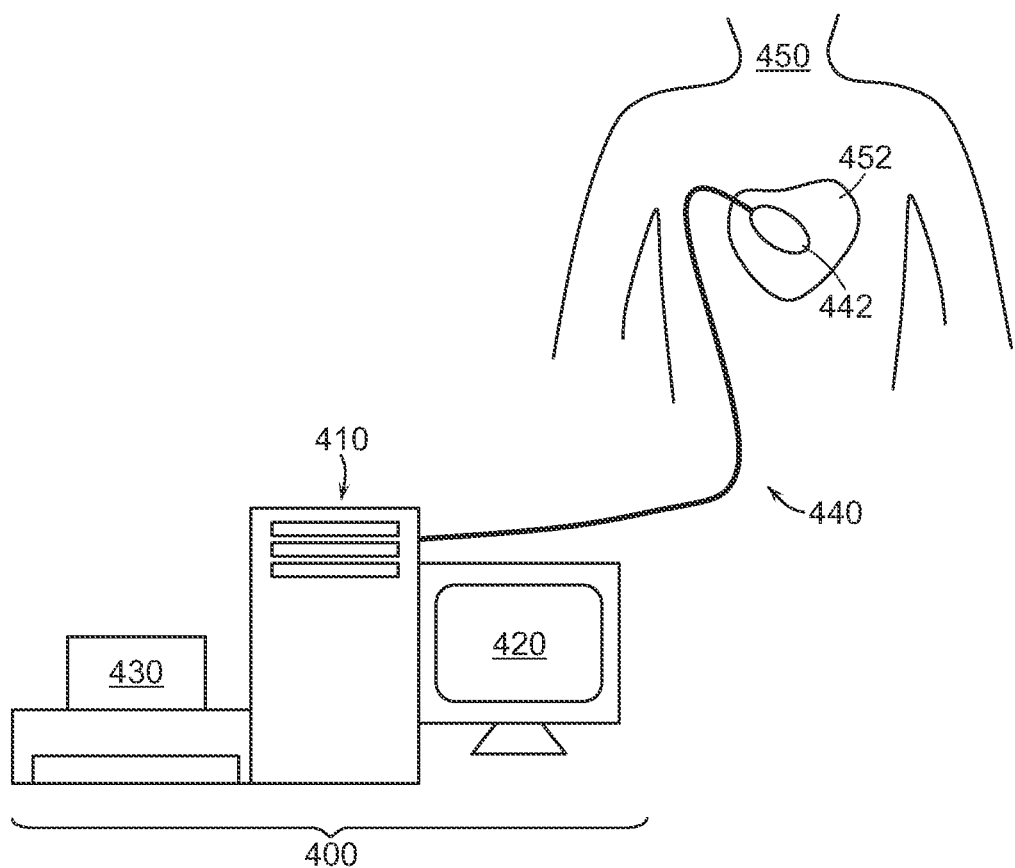
FIG. 4 is an exemplary embodiment of a system for determining a database table of dipole and/or surface charge densities and for displaying such density information, in accordance with aspects of the present invention.

FIG. 4 shows an example embodiment of a system 400 configured to determine a database table of dipole and/or surface charge densities of at least one heart chamber of a patient, e.g., as an embodiment of system 300 above. That is, system 400 can be considered to be a somewhat simplified version of system 300, used to describe an approach for determining dipole and/or surface charge densities using voltage measurements representing cardiac activity. System 400 can be used to map activity of a heart 452 of a patient 450, e.g., a human. In order to generate a map of surface charge densities (e.g., a surface charge density distribution), the geometry of the given heart chamber is determined or obtained in any of a variety of manners such as those described herein. The multi-dimensional geometry of the cardiac chamber can be assessed, in various embodiments, by currently available and common mapping systems (so-called locator systems) or, alternatively, by integrating anatomical data from CT/MRI scans.

System 400 can include a computer 410 having known types of input devices and output devices, such as a display 420 and printer 430, and a probe system 440. For the measurement of potentials, contact and/or non-contact mapping methods can be used. The mapping methods can use a probe electrode system 442, which is connected to the computer 410 via a cable and forms part of probe system 440 as shown in FIG. 4. Probe system 440 can take the form of, or include, a catheter. The computer 410 can be configured to include at least one processor and computer storage device, comprising a set of executable functional modules that perform various tasks to determine dipole and/or surface charge density using cardiac potential information from the probe system 440.

The probe electrode 442 can take the form of a multi-electrode array with elliptic or spherical shape, in some embodiments. The spherical shape of such an array can have certain advantages for the subsequent data analysis. Alternatively or additionally, other types or even several independent electrodes could be used to measure $V_e$ (i.e., the voltage on the endocardium). For example, when considering a cardiac cavity within the endocardium and taking a probe electrode with a surface $S_P$, which is located in the blood (i.e. non-contacting), it is possible to measure the potential V(x,y,z) at point x,y,z on the surface $S_P$. In order to calculate the potential at the endocardial surface $S_e$ the Laplace equation:

$$\Delta V = \left(\frac{\partial^2}{\partial x^2} + \frac{\partial^2}{\partial y^2} + \frac{\partial^2}{\partial z^2}\right)V = 0 \qquad (4)$$

needs to be solved, wherein V is the potential and x,y,z denote the three dimensional coordinates. The boundary conditions for this equation are $V(x,y,z)=V_P(x,y,z)$ on $S_P$, wherein $V_P$ is the potential on surface of the probe $S_P$.

The solution is an integral that allows for calculating the potential V(x'y'z') at any point x'y'z' in the whole volume of the heart chamber that is filled with blood. For calculating said integral numerically, a discretization of the cardiac surface is necessary and the so called boundary element method (BEM) can be used.

The boundary element method is a numerical computational method for solving linear integral equations (i.e. in surface integral form). The method is applied in many areas of engineering and science, including fluid mechanics, acoustics, electromagnetics, and fracture mechanics.

The boundary element method is often more efficient than other methods, including the finite element method. Boundary element formulations typically give rise to fully populated matrices after discretization. This result means that the storage requirements and computational time, using BEM, will tend to grow according to the square of the problem size. By contrast, finite element matrices are typically banded (elements are only locally connected) and the storage requirements for the system matrices typically grow quite linearly with the problem size.

With the above in mind, all potentials $V_P(x1',y1',z1')$ on the surface of the probe can be measured. To calculate the potential $V_e$ on the wall of the heart chamber, the known geometry of the surface of the heart chamber are divided into discrete parts to use the boundary element method. The endocardial potentials $V_e$ are then given by a linear matrix transformation T from the probe potentials $V_P$: $V_e = TV_P$.

After measuring and calculating one or more electric potential(s) $V_e$ of cardiac cells in one or more position(s) P(x,y,z) of the at least one given heart chamber at a given time t, the surface charge and/or dipole densities are determined. The surface charge density and the dipole density are related to potential according to the following two Poisson equations:

$$\Delta V_e = \rho(P)\delta_{S_e}(P) \qquad (5)$$

$$\Delta V_e = \frac{\delta}{\partial n}(\upsilon \delta_{S_e}(P)) \qquad (6)$$

wherein ρ(P) is the surface charge density in position P=x,y,z, $\delta_{S_e}$ (P) is the delta-distribution concentrated on the surface of the heart chamber $S_e$ and υ is the dipole density.

A relationship exists between the potential $V_e$ on the surface of the wall of the heart chamber and the surface charge (7) or dipole densities (8).

$$V_e(P) = -\frac{1}{4\pi}\int_{S_e} \frac{\rho(P')}{|P'-P|} d\sigma(P') \qquad (7)$$

$$V_e(P) = \frac{1}{4\pi}\int_{S_e} \upsilon(P')\frac{\partial}{\partial n_{P'}} \frac{1}{|P-P'|} d\sigma(P') \qquad (8)$$

(For a review see Jackson J D. *Classical Electrodynamics*, 2$^{nd}$ edition, Wiley, New York 1975.)

The boundary element method again provides a code for transforming the potential $V_e$ in formulas 7 and 8 into the desired surface charge densities and dipole densities, which can be recorded in a database of surface charge densities and/or dipole densities.

In another embodiment, the electric potential(s) $V_e$ is (are) determined by contact mapping. In this case the steps for calculating the electric potential $V_e$ are not necessary, because the direct contact of the electrode to the wall of the heart chamber already provides the electric potential $V_e$.

In an example embodiment, the probe electrode comprises a shape that allows for calculating precisely the electric potential $V_e$ and, thus, simplifies the calculations for transforming $V_e$ into the desired charge or dipole densities. That is, the geometry of the electrode can be ellipsoidal or spherical in such an embodiment.

In order to employ the method for determining a database (or table) of surface charge densities of at least one given heart chamber in the context of the present invention, a system comprising at least the following can be used:

a) one unit for measuring and recording electric potentials V at a given position P(x,y,z) on the surface of a given heart chamber (contact mapping) or a probe electrode positioned within the heart, but without direct wall contact (noncontact mapping)

b) one a/d-converter for converting the measured electric potentials into digital data, c) one memory (e.g., computer memory) to save the measured and/or transformed data, and d) one processor unit for transforming the digital data into digital surface charge density or dipole density data.

It is noted that numerous devices for localizing and determining electric potentials of cardiac cells in a given heart chamber by invasive and non-invasive methods are well known in the art and have been employed by medical practitioners over many years. Hence, the present invention is not limited to any particular types of electrodes or other sensors or transducers. Instead, the invention provides a new and advantageous processing of the available data that will allow for an increase in precision, accuracy and spatial resolution of cardiac activation mapping when compared to prior art systems based on electric surface potentials in the heart only. The present invention provides enhanced diagnostic means for diagnosing cardiac diseases and disorders (e.g. arrhythmias) and other electric status of heart cells including metabolic and functional information.

Catheters and other devices as used in the context of the present invention can include numerous forms of diagnostic catheters such as catheters including one or more electrodes, or therapeutic catheters such as tissue ablation catheters, such as, for example, the catheters described in U.S. patent application Ser. No. 14/422,941, filed Feb. 5, 2015, entitled Catheter System and Methods of Medical Use of Same, Including Diagnostic and Treatment Uses for the Heart. Catheters can be introduced percutaneously into a patient's heart, such as to record electrical activity, measure distances between structures, or deliver energy. External devices and systems can be included, such as body surface electrodes used to record an electrical signal and/or deliver an electric signal, or visualization devices such as external ultrasound or fluoroscopic imaging systems. Any of these catheters or other devices can include one or more electrodes, one or more ultrasound transducers, and/or one or more other sensors or transducers. These electrodes, ultrasound transducers, and/or other sensors or transducers can be positioned at any location on the device, for example at a distal or proximal portion of the device, and can be positioned internal or external to a patient's body.

Any or all of the ultrasound transducers can be used to measure a distance between the transducer and a surface, as is known in the art. One example includes measuring the distance between the ultrasound transducer and a wall of the cardiac chamber. Another example includes measuring the distance between the ultrasound transducer and a component of the same or a separate device.

Any or all of the electrodes of such catheters can be used to record electric "signals" (e.g. voltages and/or currents) at or between the electrode locations. Recorded electric signals can be used to map electrical activity of tissue, such as when an electrode is positioned away from tissue (e.g. in the circulating blood) or when an electrode is in contact with tissue. Algorithms, such as those described hereabove, can be used to correlate recorded signals at multiple non-contacting locations to signals present at one or more tissue locations. The mapped electrical activity and/or other electrical signals can be further processed (e.g. in terms of sources of charge and charge density and correlated with various physiologic parameters related to the function of the heart) and the mapped electrical activity and other recorded and calculated information can be provided visually to one or more operators of the system of the present invention.

Any or all of the electrodes can be used to deliver and/or record electric signals that are generated by the system. Such delivered signals can be emitted from any one or more electrodes, and can be delivered between any two or more electrodes. Recorded signals can comprise a signal present at a single electrode location or at multiple electrode locations (e.g. a signal representing a comparison of two or more signals present at two or more electrode locations). Recorded signals can be measured, for example, synchronously or asynchronously in terms of voltage and/or current. Recorded signals can be further processed in terms of, for example, resistive and reactive components of impedance and/or the combined magnitude of impedance with any original or processed signal "values" (e.g. those represented by a parameter selected from the group consisting of: instantaneous amplitude; phase; peak; Root-Mean-Square; demodulated magnitude; and combinations of these).

Referring now to FIGS. 5A and 5B, perspective views of the distal portion of a system for diagnosing and/or treating a heart disease or disorder, such as atrial fibrillation and/or ventricular tachycardia, is illustrated. The system can be an embodiment of array 315 of FIG. 3, array 530' of FIG. 5C, and/or probe electrode system 442 of FIG. 4, or portions thereof. FIG. 5A illustrates an ablation catheter slidingly received by the shaft of a diagnostic catheter and FIG. 5B illustrates the ablation catheter of FIG. 5A in a bent configuration, in accordance with aspects of the present invention.

The probe system 440 includes a diagnostic catheter 500 which is constructed and arranged for insertion into a body location, such as the chamber of a heart. Catheter 500 includes shaft 502, typically constructed of sufficiently flexible material to allow insertion through the tortuosity imposed by the patient's vascular system. On the distal portion of shaft 502 is an expandable assembly 530, which includes a plurality of electrodes 541 coupled thereon. Additionally, a plurality of ultrasound transducers 551 are coupled to expandable assembly 530 in this embodiment. Electrodes 541 and USTs 551 are each electrically attached to one or more wires which travel proximally within shaft 502, connecting to one or more receivers such as receivers 110 and 120 described hereabove in reference to FIG. 1. In some embodiments, catheter 500, expandable assembly 530, electrodes 541 and/or ultrasound transducers 551 are constructed and arranged as the similar components described in Applicant's co-pending U.S. patent application Ser. No. 14/003,671, entitled Device and Method for the Geometric Determination of Electrical Dipole Densities on the Cardiac Wall, filed Sep. 6, 2013, the entirety of which is incorporated herein by reference. The number and pattern of electrodes (or other sensors) and USTs can be different in different embodiments; the invention is not limited to the embodiment depicted in FIGS. 5A and 5B which includes a pattern of two electrodes 541 between pairs of USTs 551. In some embodiments, a repeating pattern of a single electrode 541 followed by a single UST 551 and so on is included, such as is shown in FIG. 5C. In some embodiments, catheter 500 can include other types of electrodes or other sensors, e.g., temperature and/or pH sensors, either in addition to or as an alternative to the electrodes shown.

The system further comprises an ablation catheter 520, which includes shaft 522. Shaft 522 includes at least one ablation element 561, located at a tip or otherwise on a distal portion of shaft 522. Ablation element 561 is constructed and arranged to deliver energy to tissue, such as when ablation catheter 520 is attached to a source of energy.

Shaft 502 includes a lumen 526 traveling from at least a proximal portion of shaft 502 (e.g. from a handle, not shown but typically positioned on shaft 502's proximal end) to a distal portion of shaft 502 (e.g. to shaft 502's distal end). Shaft 502 of ablation catheter 520 and lumen 526 of diagnostic catheter 500 are constructed and arranged to allow shaft 522 of ablation catheter 520 to be slidingly received by lumen 526. Lumen 526 can be further configured to slidingly receive additional catheters or other elongate devices, such as prior to insertion of diagnostic catheter 500 into a body, or after diagnostic catheter 500 has been inserted into a body.

Diagnostic catheter 500 can be used for mapping tissue such as an organ or portion of an organ (e.g. a portion of a heart wall). Multi-dimensional anatomical mapping information collected by diagnostic catheter 500 can be used by the system (e.g., computer system 400) to create a multi-dimensional display of an anatomical location of which at least a portion is to be treated by ablation catheter 520. Diagnostic catheter 500 can be coupled to a computer system, e.g., computer system 400) configured to display anatomical mapping information generated by diagnostic catheter 500, such as volumes, locations, shapes, contours, and movement of organs, nerves, and other tissue within the body. Diagnostic catheter 500 can be coupled to the computer system 400 to display the electrical mapping information generated by diagnostic catheter 500, such as to display dipole mapping or other information as has been described above. Additionally, the location of ablation catheter 520 or other inserted devices can be displayed, such as their position relative to tissue or diagnostic catheter 500. For example, diagnostic catheter 500 can be used to map the heart, while ablation catheter 520 can be directed to a tissue location in the heart targeted for treatment (e.g. targeted for treatment based on information provided by diagnostic catheter 500 and/or another component of system 400). For example, ablation catheter 520 can be configured to ablate cardiac tissue to treat a patient suffering from a cardiac arrhythmia, such as atrial fibrillation, atrial flutter, supraventricular tachycardias (SVT), Wolff-Parkinson-White syndrome, and ventricular tachycardias (VT). An ablation catheter will be described herein as a form of a treatment device for purposes of conveying aspects of the invention, but a different type of treatment device (e.g., a pacing device; a defibrillation device; a stent delivery device; a drug delivery device, a stem cell delivery device, or the like) can be used in other embodiments in combination with diagnostic catheter 500. In some embodiments, one or more of these treatment devices is inserted through a lumen of diagnostic catheter 500.

In some embodiments, the system is configured to access the left atrium of the patient while utilizing a single transseptal puncture through which all the catheter components of system access the left atrium (and subsequently the left ventricle in some cases). In other embodiments, the system is configured to access the left ventricle of the patient while utilizing a single crossing of the aortic valve through which all the catheter components of the system access the left ventricle (and subsequently the left atrium in some cases).

The system can include sheath 504, for example a standard access sheath, such as a standard transseptal access sheath. In some methods, sheath 504 can be inserted through the atrial septum and into the left atrium, followed by the insertion of diagnostic catheter 500 through a lumen of sheath 504. Subsequently, ablation catheter 520 can be inserted through lumen 526 of diagnostic catheter 500. In other methods, sheath 504 is inserted into the left atrium, followed by the simultaneous insertion of diagnostic catheter 500 and ablation catheter 520 (e.g. diagnostic catheter 500 is inserted with ablation catheter 520 residing at least partially within lumen 526). In some embodiments, sheath 504 can comprise a steerable sheath. Shaft 502 comprises a diameter along the majority of its length such as to be slidingly received by sheath 504. In some embodiments, shaft 502 comprises a diameter less than or equal to 15 Fr. In some embodiments, diagnostic catheter 500 and/or ablation catheter 520 can be steerable, so that manual, semiautomatic or automatic steering can be performed by an operator and/or a robotic control assembly of the system, as shown in FIG. 5B.

Diagnostic catheter 500 can be positioned in the left atrium and can provide information selected from the group consisting of: electrical information, such as voltage information (e.g. voltage information which is analyzed to produce surface charge information); anatomical geometry information, such as heart wall surface information or heart wall thickness information; other physiologic and anatomical information, such as those described herein; and combinations of these. Shaft 502 of diagnostic catheter 500 can be configured to be inserted into the heart via the venous system, for example a vein in a leg or a vein in a neck. Shaft 502 can include a braid within its outer and inner surfaces, not shown but typically a braid of plastic or metal fibers that enhance the structural integrity and performance of shaft 502. In some embodiments, the braid of shaft 502 can include conductors (e.g. one or more conductors connected to an electrode 541 and/or an ultrasound transducer 551).

As described above, diagnostic catheter 500 includes lumen 526 extending from a proximal portion to a distal portion of shaft 502, for example from a proximal end to a distal end of shaft 502 so as to allow a separate catheter or other elongate device to be inserted therethrough, such as ablation catheter 520, as shown. Alternatively or additionally, the inserted catheter or other elongate device can include a diagnostic catheter, such as a diagnostic catheter configured to record signals from a location selected from the group consisting of: the left atrium; the right atrium; the Bundle of HIS; the right ventricular apex; a pulmonary vein;

the coronary sinus. Alternatively or additionally, the inserted catheter can comprise another catheter device.

Diagnostic catheter 500 can include expandable assembly 530, which is positioned at the distal end of shaft 502—here in the form of a basket array. As illustrated, expandable assembly 530 includes an array of splines 531, each spline 531 having proximal segment 532, middle portion 534, and distal segment 533. Proximal segment 532 of each spline 531 connects to shaft 502, via connection point 527. The distal ends of each spline 531 connect in a circumferential ring configuration to form opening 535. Opening 535 allows a device to pass through, such as a device inserted into lumen 526, for example shaft 522 of ablation catheter 520. In some embodiments, expandable assembly 530 can include one or more guide elements configured to guide a device through opening 535.

Expandable assembly 530 can be constructed and arranged to be positioned in the expanded shape shown in FIGS. 5A and 5B. The expanded geometry of assembly 530, including at least two or more splines 531 in an expanded or partially expanded state (hereinafter "expanded state"), can be described as a "basket" having a substantially hollow center and spaces between adjacent splines 531. In the illustrated embodiment, the basket is spherical, but can include any suitable shape, for example an ellipsoid or other symmetric or asymmetric shape. Thus, in other embodiments, assembly 530 can comprise different shapes or combination of shapes, such as an array of splines 531 where two or more splines 531 comprise similar or dissimilar shapes, dimensions or configurations. In some embodiments, two or more splines 531 include a varied radius of curvature.

Expandable assembly 530 can be biased in an expanded or non-expanded state. In an example embodiment, assembly 530 can be self-expanding such that splines 531 are resiliently biased in the curved geometry shown in FIGS. 5A and 5B. Assembly 530 can automatically expand when assembly 530 exits the distal end of sheath 504, such as by advancement of shaft 522 and/or retraction of sheath 504. Alternatively, assembly 530 can be manually expanded, for example via retraction of a rod (not shown) that slides within shaft 502 and is connected to distal end of assembly 530.

Splines 531 can be constructed of a material selected from the group consisting of: one or more thermoplastic polymers such as polyether block amide, polyurethane and/or polyether ether ketone; one or more of thermoset polymers such as silicon and/or tetrafluoroethylene; one or more metals such as stainless steel and/or shape memory alloys such as nickel titanium alloy; one or more shape memory polymers such as triple shape acrylic; and combinations of these. Generally, any of a number of materials or compositions that are biocompatible, flexible or bendable, and possess any necessary application specific electrical properties can be used for splines 531.

Splines 531 can include one or more electrodes 541 and/or one or more ultrasound transducers 551 arranged in any combination. For example, in some embodiments, one or more of the following configurations is included: each spline 531 includes at least four, six or eight electrodes 541; each spline 531 includes at least four, six or eight ultrasound transducers 551; and combinations of these. In some embodiments, at least one electrode 541 is positioned between two ultrasound transducers 551 on a single spline 531 (such as in the alternating pattern shown in FIG. 5C). In some embodiments, at least two electrodes 541 are positioned between two ultrasound transducers 551 on a single spline 531.

Each spline 531 can include a similar or dissimilar arrangement of electrodes 541 and/or ultrasound transducers 551 such as an adjacent spline 531 or any other spline 531 in assembly 530. In some embodiments, assembly 530 includes eight splines 531, where each spline 531 can include two to eight electrodes 541 and two to eight ultrasound transducers 551. In some embodiments, assembly 530 includes six splines 531, where each spline 531 can include eight electrodes 541 and eight ultrasound transducers 551. In some embodiments, one or more splines 531 include a number of electrodes 541 that comprises a quantity within one of the quantity of ultrasound transducers 551 that are included on that spline 531. For example, a spline 531 can include seven electrodes 541 and either six or eight ultrasound transducers 551. In some embodiments, a set of electrodes 541 and ultrasound transducers 551 can be arranged in an alternating arrangement, such that one or more single ultrasound transducers 551 lies between two electrodes 541. In some embodiments, some sets of electrodes 541 and ultrasound transducers 551 can be arranged such that one or more single electrodes 541 is positioned between two ultrasound transducers 551.

Electrodes 541 can be configured to record electric signals such as voltage and/or current signals. The system can utilize the recorded signals to produce electrogram information; dipole mapping information; surface charge information; distance information such as the distance between any device and/or component of the system; and other information or combinations of information described in detail herein. Any or all electrodes 541 can comprise a dipole and/or surface charge mapping electrode, such as an electrode with an impedance or other electrical property configured to provide information related to surface charge or other dipole mapping parameter. In some embodiments, the electrodes 541 are of sufficiently low impedance, such as in the range less than 10,000 ohms, such as to achieve high-fidelity recording of signal frequencies greater than or equal to 0.1 Hz. In some embodiments, one or more electrodes 541 include an iridium oxide coating, such as to reduce the impedance of electrodes 541. Alternatively or additionally, numerous forms of coatings or other treatments can be included with one or more electrodes 541, such as a platinum black coating or a carbon nanotube layer. In addition or as an alternative to recording electric signals, electrodes 541 can be constructed and arranged to deliver electric energy, such as radiofrequency energy. In some embodiments, diagnostic catheter 500 can deliver therapy, such as an ablation therapy delivered to tissue, in addition to its function as a diagnostic catheter, e.g. providing electrical, anatomical and/or device mapping information. In some embodiments, one or more electrodes 541 each comprise one or more coils, such as when the one or more coils are configured to create one or more magnetic fields.

Electrodes 541 can include various materials such as non-polarizing metals and/or polarizing metals. In some embodiments, one or more electrodes 541 comprise at least one non-noble metal such that electrodes 541 oxidize when in contact with at least one of blood, blood plasma or saline solutions. In some embodiments, electrodes 541 include a coating, for example a coating selected from the group consisting of: a metal oxide coating; a conductive polymer coating; and combinations of these. In some embodiments, one or more electrodes 541 can include an outer layer and an inner layer, such as when the outer layer comprises an impedance lowering coating or other layer and the inner layer comprises a layer configured to bond the outer layer to the metallic and/or other remaining portion of the one or more electrodes 541.

Ultrasound transducers 551 can be configured to record distance information such as the distance between any device and/or component of the system and tissue such as cardiac wall or other solid tissue. Ultrasound transducers 551 can include a construction comprising: single or multi-element piezoelectric ceramics; piezoelectric micro-machined ultrasound transducers (pMUT); capacitive micro-machined ultrasound transducers (cMUT); piezoelectric polymers; and combinations of these.

In some embodiments, diagnostic catheter 500 can include a multi-layer or laminate construction, for example where shaft 502 includes a tube inside of another tube; where shaft 502 includes a liner such as a liner constructed of a lubricous material such as PTFE; where shaft 502 includes a braided construction such as a braid positioned between two layers of shaft 502; and combinations of these. In some embodiments, diagnostic catheter 500 can be steerable, for example via the incorporation of a pull wire and anchor (not shown). Typically, diagnostic catheter shaft 502 outer diameter is less than 15 Fr.

Ablation catheter 520 of FIGS. 5A and 5B includes ablation element 561 positioned on shaft 522, for example on a distal portion or the distal tip of shaft 522. Ablation element 561 can include a functional element selected from the group consisting of: one or more electrodes; a vessel or port configured to deliver cryogenic energy; a laser diode; an optical fiber configured to deliver ablative light energy; a microwave energy delivery element; an ultrasound energy delivery element; a drug, stem cell, or other agent delivery element; an abrasive or other mechanical ablative energy delivery element; and combinations of these. In the case where ablation element 561 includes one or more electrodes, the electrodes can include electrodes constructed and arranged to deliver radiofrequency (RF) energy. In the case of multiple electrodes, the electrodes can be configured for monopolar and/or bipolar RF energy delivery. In some embodiments, ablation element 561 can include an array of elements. Ablation catheter 520 can be operably connected to a device configured to deliver energy to ablation element 561, such as ablation source 230 of FIG. 3. Typical energy delivered by ablation element 561 comprises an energy selected from the group consisting of: electromagnetic energy such as radiofrequency energy; cryogenic energy; laser energy; light energy; microwave energy; ultrasound energy; chemical energy; and combinations of these.

In FIG. 5B, ablation catheter 520 can be steerable, similar to diagnostic catheter 500 and sheath 504, such as via a pull wire and anchor. Here, ablation catheter 520 has been steered in a curved geometry 525, as shown, to cause ablation element 561 to exit expandable assembly 530 of diagnostic catheter 500, passing between two middle portions 534 of two splines 531. Ablation catheter 520 can be steered and advanced by an operator such as a clinician, so as to exit at any opening of the expandable assembly 530, including the space between two splines 531 or through opening 535, such as to be further advanced to contact or move proximate to cardiac tissue, e.g., for ablation.

Various timing sequences can be used for sending and/or recording signals to and/or from electrodes 541 and/or USTs 551 on splines 531 of expandable assembly 530 in FIGS. 5A and 5B. In the preferred embodiment, a timing sequence is used that provides a pattern of "ringing" the USTs that alternates between splines. The timing sequence can also include timing of driving some of the spline electrodes and skin patch electrodes (optionally included) for localization. In some embodiments, electrodes 541 are continuously recorded. In some embodiments, an electrode 541 and a UST 551 share a common conductor, and an electrode 541 does not record when the UST 551 sharing the common conductor is receiving a ring signal. The timing sequence of sending and/or recording signals can be computer controlled. A full cycle of a timing sequence can be, for example, 100 ms or less (e.g. a cycle in which a series of sequential ring signals are sent to each UST 551). In some embodiments, a timing sequence is modified over time, such as to change the time of a full cycle and/or to modify the order in which signals are sent (e.g. to ring a UST 551) or recorded (e.g. from an electrode 541).

Referring now to FIG. 5C, a perspective view of an alternative layout of electrodes and ultrasound transducers (USTs) positioned on an expandable array is illustrated, in accordance with aspects of the present invention. Probe system 440 includes mapping catheter 500' and sheath 504 through which the distal portion of mapping catheter 500' has been inserted. Mapping catheter 500' includes array 530' positioned on the distal end of shaft 502'. Array 530' comprises multiple splines 531 upon which an alternating pattern of a single electrode 541 followed by a single UST 551 is positioned, as shown. Electrodes 541 and USTs 551 are each electrically attached to one or more wires which travel proximally within shaft 502', connecting to one or more receivers such as receivers 110 and 120 described hereabove in reference to FIG. 1. System 440 can include an ablation catheter, such as an ablation catheter similar to ablation catheter 520 of FIGS. 5A and 5B. The ablation catheter can be advanced into the heart alongside shaft 502' and sheath 504. In some embodiments, shaft 502' comprises a lumen, such as shaft 502 of FIGS. 5A and 5B, through which an ablation catheter or other device can be inserted.

Figure 6:
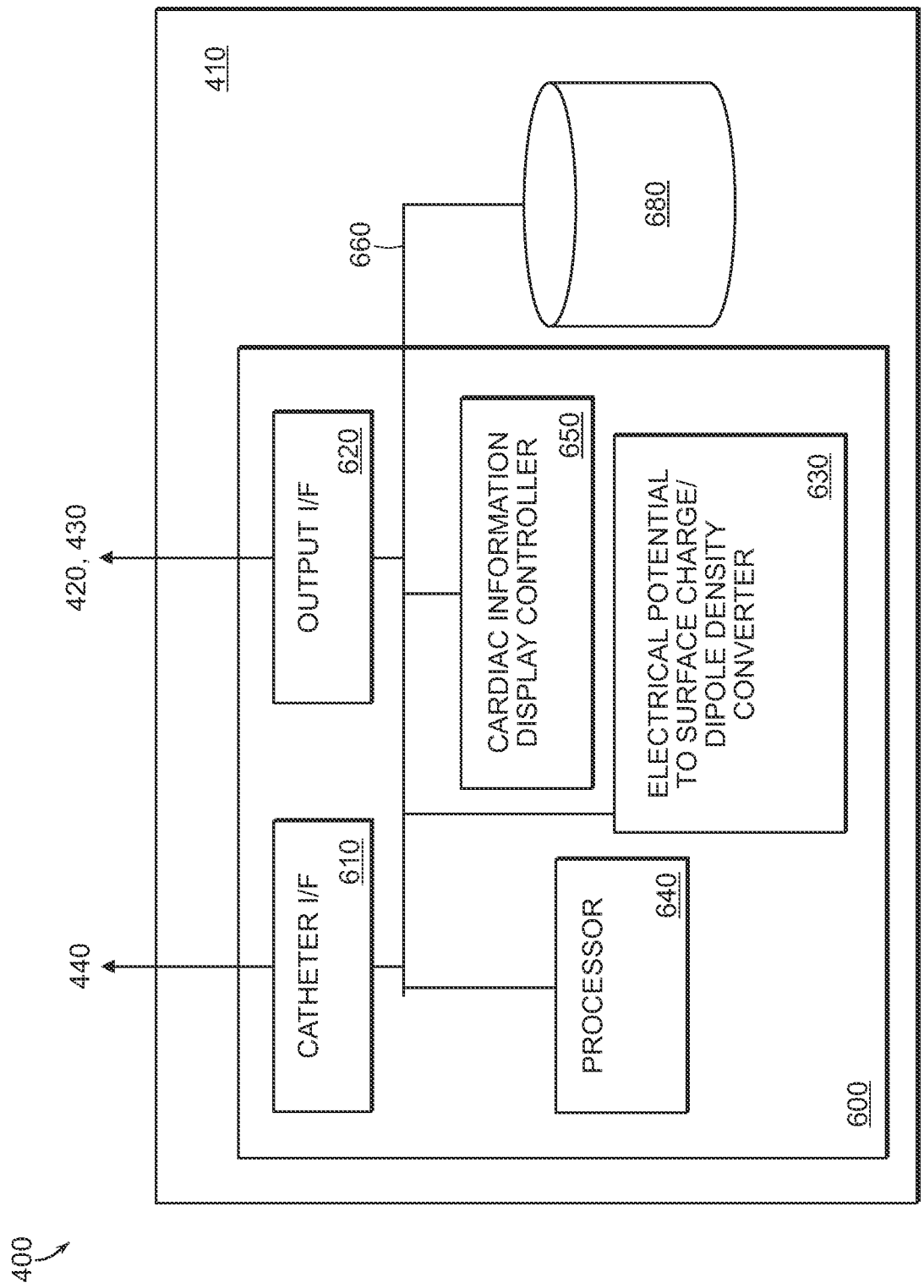
FIG. 6 is an exemplary embodiment of a computer architecture forming part of the system of FIG. 4, in accordance with aspects of the present invention.

FIG. 6 provides an example embodiment of a computer architecture 600 that can form part of system 400 configured to determine a database table of dipole densities of at least one heart chamber of a patient, which can communicate with the probe system 440 of FIGS. 4, 5A and/or 5C, as examples. Architecture 600 can include standard interface modules 610 for probe system 440 (and electrodes 442 and/or catheters 500, 500' and 520) and interface modules 620 for interfacing with output devices 420, 430. Architecture 600 can further include cardiac information display controller 650 for receiving, interpreting, generating, processing and/or providing cardiac information. The computer 410 includes at least one processor 640 and at least one computer memory 680 connected to elements 610, 620, 630, 640 and/or 650 via bus 660 as shown. The architecture 600 further includes an electrical potential to surface charge density and/or dipole density converter module 630. Module 630 includes executable computer instructions necessary for carrying out the methods described herein, when executed by processor 640, wherein the results of such processing are stored in memory (e.g., a database, data storage system, or data storage device) 680— as would be understood by one skilled in the art having the benefit of this disclosure. That is, module 630 is preferably configured to determine dipole and/or surface charge densities from data received, at least in part, from probe system 440, as described herein or otherwise.

Figure 7:
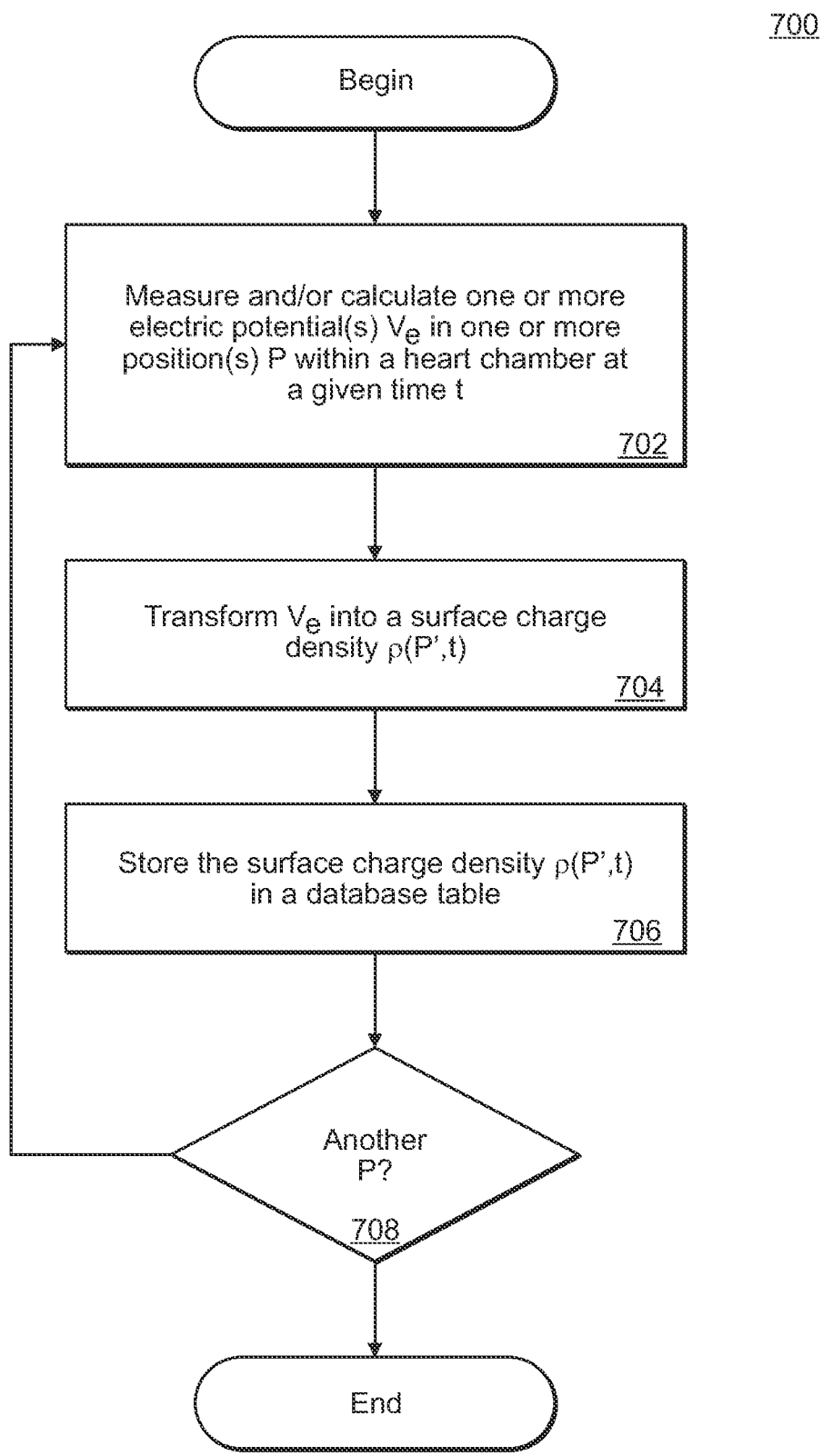
FIG. 7 is an example embodiment of a method of determining and storing surface charge densities, in accordance with aspects of the present invention.
Figure 8:
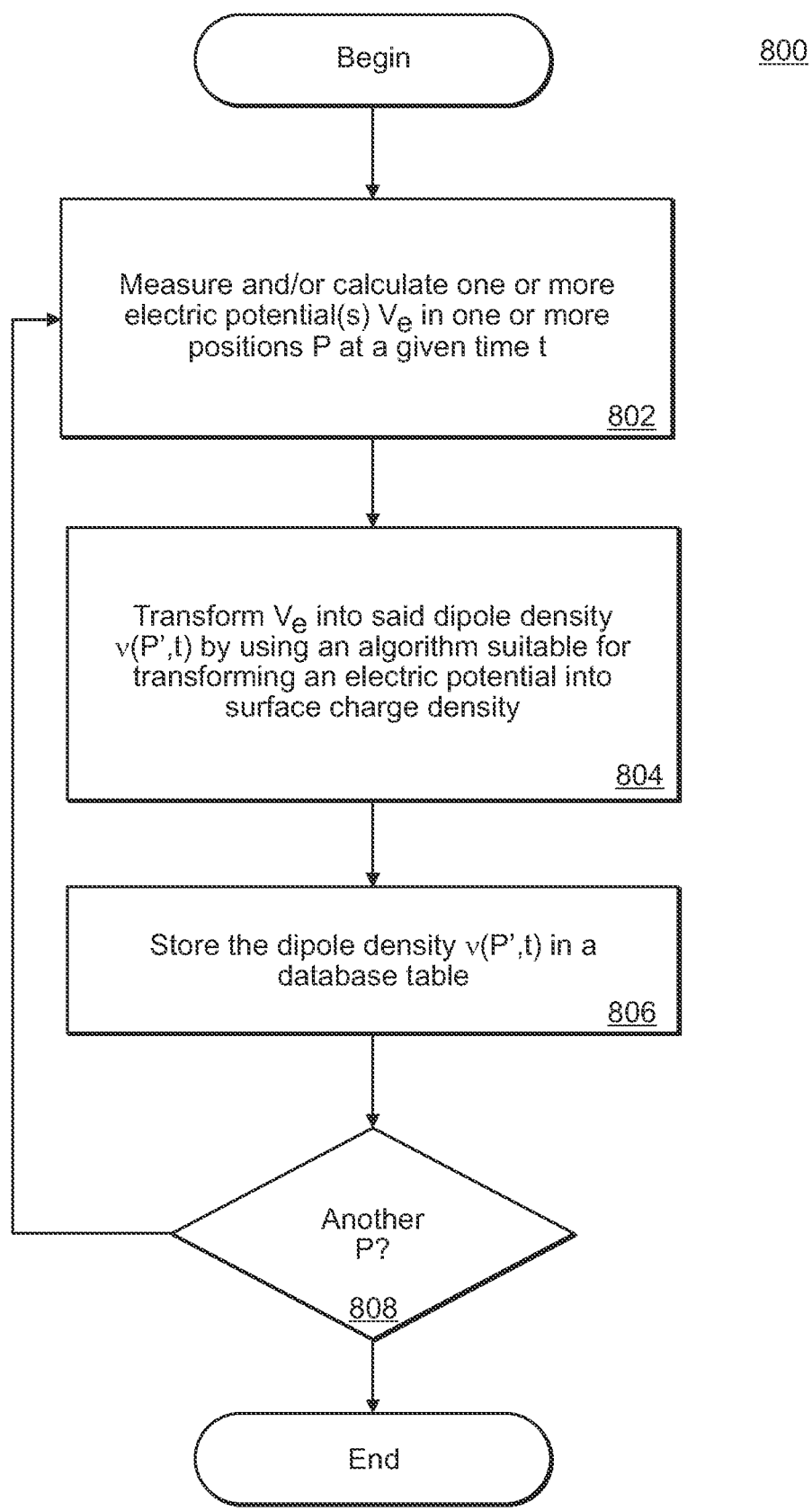
FIG. 8 is an example embodiment of a method of determining and storing dipole densities, in accordance with aspects of the present invention.

FIG. 7 and FIG. 8 summarize embodiments of methods for determining and storing surface charge densities and dipole densities in accordance with aspects of the present invention, respectively, which have been described in detail above.

In method 700 of FIG. 7, in Step 702, system 400 is used to measure and/or calculate one or more electric potential(s) $V_e$ into one or more position(s) P within a heart chamber at a given time t. In Step 704, $V_e$ is transformed into a surface charge density ρ(P',t). In Step 706, the surface charge density ρ(P',t) is stored in a database table. The method is repeated if there is another P, in Step 708.

In method 800 of FIG. 8, in Step 802, mapping system 400 is used to measure and/or calculate one or more electric potential(s) $V_e$ in one or more position(s) P within a heart chamber at a given time t. In Step 804, $V_e$ is transformed into said dipole density v(P',t) by using an algorithm suitable for transforming an electric potential into surface charge density. In Step 806, the dipole density v(P',t) is stored in a database table. The method is repeated if there is another P, in Step 808.

In accordance with aspects of the present invention, the architecture 600 further includes a cardiac information display (CID) controller 650. In this embodiment, CID controller 650 is configured to generate and/or provide information sufficient for at least one display device to render cardiac information, which can include, but is not limited to, dipole density and/or surface charge density information. The cardiac information could also include cardiac voltage (or potential) information, a graphical model of a heart or portion of a heart (or other organ), images of a heart or portions thereof (or other organ), other local information such as temperature and/or pH information, other field information (e.g. other than voltage information), or combinations thereof. The rendering of the heart and/or portion of the heart (or other organ) could be two-dimensional (2-D), three-dimensional (3-D), or combinations thereof. Such cardiac information can also include an electrocardiogram (EKG or ECG), e.g., such as a graph of the heart's electrical activity versus time. The above types of cardiac information could be displayed in various combinations, e.g., to include dipole density and/or surface charge density information, and displayed in 2-D, 3-D, or combinations thereof.

Such cardiac information could be stored in memory 680 for real-time, near real-time, or subsequent display. The display could be a computer monitor, tablet, smartphone, television, or other type of display device or device comprising such a display. The display(s) could be local, remote, or combinations thereof (if more than one display). The display(s) could be wired, wireless, or combinations thereof (e.g. if more than one).

For purposes of describing the differences in the display of information, different types of information can be distinguished. For example, dipole and charge density information is different from voltage (or potential) information. For example, dipole and charge density information, e.g., from methods 700 and 800, can be considered to be types of "source information," which is data representing, at a location in 3D space, a physical property or properties discrete to the specific location in 3D space, e.g., similar to temperature or pH information which is also source information. In contrast, voltage (or potential) information can be considered to be "field information," which is data representing, at a location in 3D space, a physical property or properties of a continuum extending through the 3D space.

Figure 9:
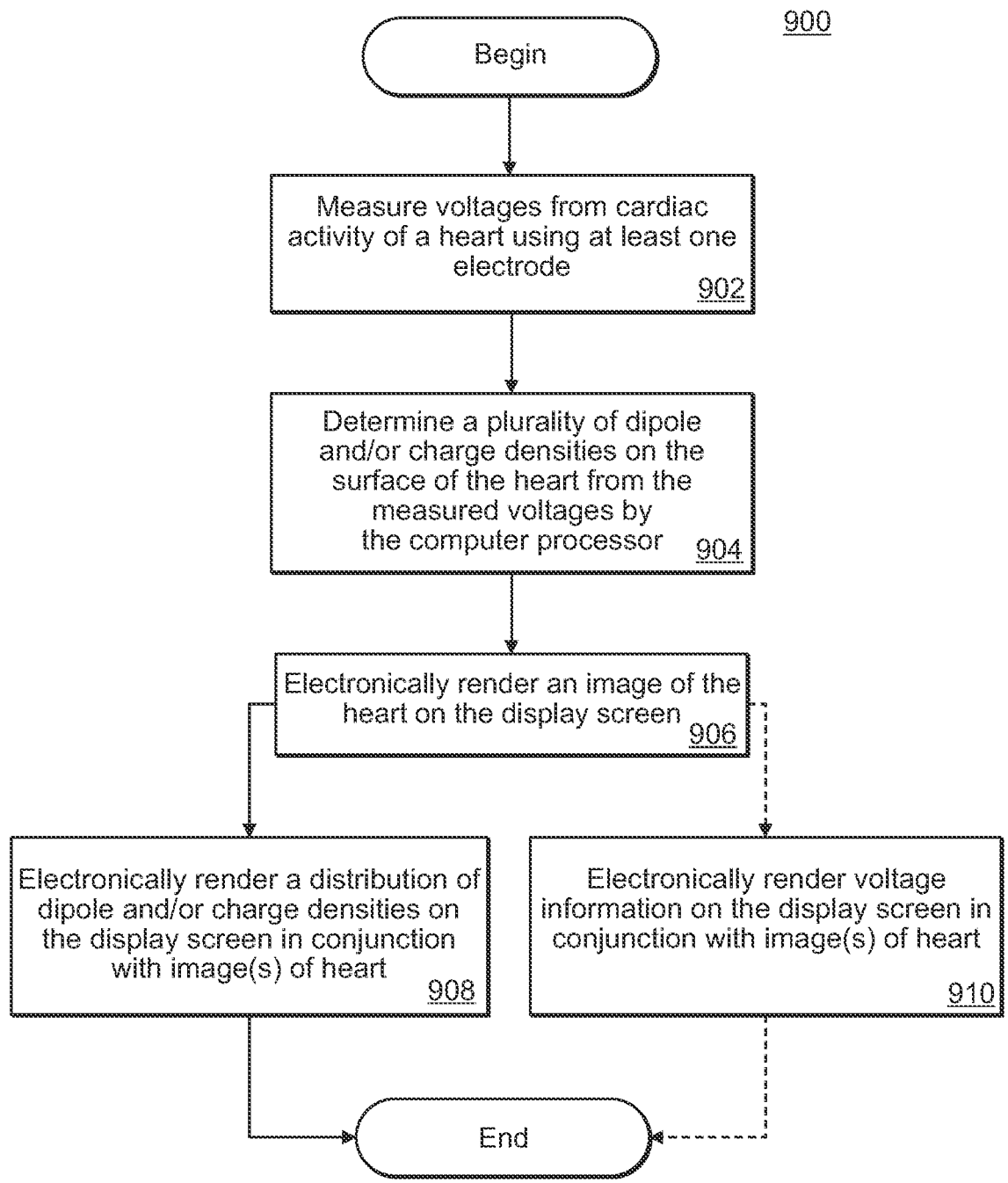
FIG. 9 is an example embodiment of a method of displaying dipole and/or surface charge densities, in accordance with aspects of the present invention.

FIG. 9 describes an embodiment of a method 900 of displaying dipole and/or charge density information in at least one electronic or computer display, preferably in conjunction with at least one image of a heart. The method can be implemented by system 400, as an example. In this embodiment, in Step 902, voltages are measured from multiple cardiac locations (e.g. within or on the endocardial surface of a heart chamber) using at least one electrode, as field information. In Step 904, from the voltages (or field information), a plurality of dipole and/or charge densities (or source information) are determined by the computer processor, e.g., on multiple locations on the surface of the heart, from the measured voltages. In Step 906, at least one image of the heart is electronically rendered on at least one (local and/or remote) display screen. In Step 908, a distribution of dipole and/or charge densities is electronically rendered on the at least one display screen, e.g., in conjunction with the image(s) of the heart. In Step 910, which is an optional step, a voltage information is electronically rendered on the at least one display screen, e.g., in conjunction with the image (s) of the heart. In various embodiments, Step 910 can be a user selectable options, wherein, for example, voltage information could be toggled on and off under the user's control.

In some embodiments, Step 902 comprises measuring voltages from an array of electrodes, serially or sequentially. In some embodiments, Step 902 further comprises moving one or more electrodes from a first location to one or more different locations and measuring voltages from the one or more electrodes at each location.

In some embodiments, Step 908 comprises rending a series of dipole and/or charge densities on the display screen, such as a series of images representing a complete cardiac cycle (i.e., heartbeat). In these embodiments, the series of images representing a complete cardiac cycle can be repeated (i.e. looped). Alternatively or additionally, the series of images representing a complete cardiac cycle can be updated (e.g. continuously updated and/or updated at discrete time intervals). In some embodiments, a series of images representing a complete cardiac cycle can be displayed with a static image of the heart (e.g. a single heart image rendered on the screen in Step 906, such as an image representing the end of systole or diastole). Alternatively, a series of images representing a complete cardiac cycle can be displayed with a corresponding series (e.g. a temporally corresponding series) of images of the heart that show the contraction and expansion of the heart during a cardiac cycle.

Figure 10:
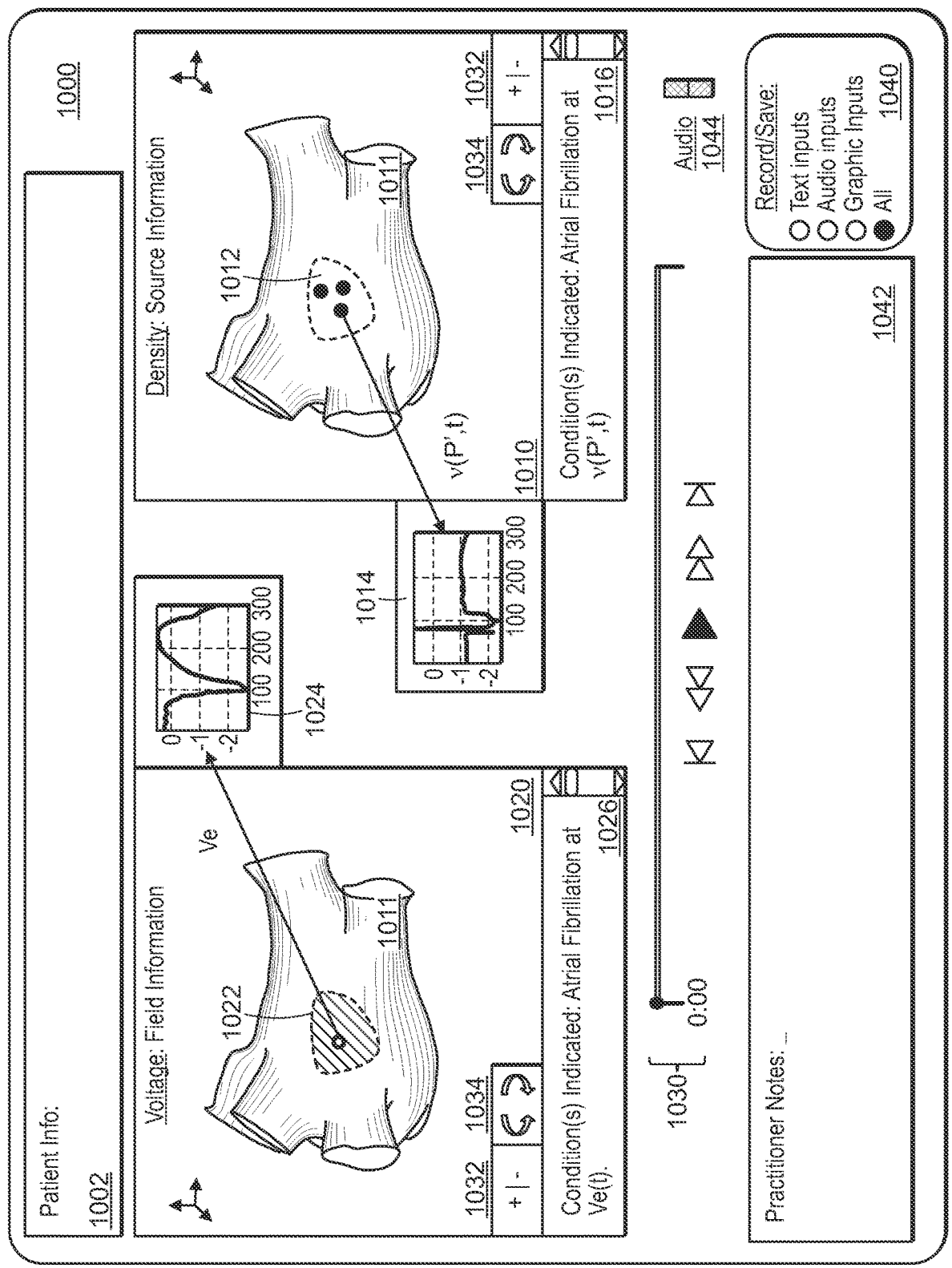
FIG. 10 is an exemplary embodiment of a user interface display of dipole and/or surface charge density information that can be generated on one or more displays, in accordance with aspects of the present invention.

FIG. 10 is an exemplary embodiment of a display 1000 of dipole and/or surface charge density information that can be generated on one or more devices, in accordance with aspects of the present invention. In this example, dipole density information is shown, but in other embodiments, additionally or alternatively, surface charge density, pH information, temperature information and/or other source or field information could be included. Display 1000 could comprise any now known or hereafter developed graphical display, such as a computer monitor, tablet, cellphone, television, display panel, Google glass, and so forth. Alternatively or additionally, information provided on display 1000 could be provided on paper such as via a printer, or sent wirelessly to a separate device. Display 1000 can include a patient information box, display area 1002 that provides relevant information about the patient (e.g. patient name, age, hospital patient ID, and the like) from whom the cardiac information was collected.

Voltage is a "force field" that spreads out from "dipolar" sources of charge, (e.g. foci in AF diagnostics), so is field information, as that term is used herein. Region of influence typically spans several centimeters in a chamber of the heart. Voltage presents a broad, blurred view of the physiologic state, similar to de-focusing a camera lens. Voltage measurements include far-field interference from adjacent locations such as adjacent chambers. In contrast, dipolar charge sources (e.g. "focal pockets") are source information, as that term is used herein, that can be derived from multiple voltage measurements (i.e., field information). Dipole and surface charge density images represent a refined, high-resolution view of physiologic information that span a very small area (e.g., —1 mm or smaller). Far-field interference from adjacent locations is reduced or eliminated. Therefore, the dipole density method is similar to re-focusing a camera lens to significantly improve resolution of local physiologic state and activity.

In this embodiment, display 1000 includes a dipole (or surface charge) density display area 1010 in which dipole (or surface charge) density information can be displayed, as a form of source information. In this example, the dipole (or surface charge) density information (v(P',t)) 1012 is displayed overlaid on an image of a heart, heart image 1011. In other embodiments, heart image 1011 is not included. Heart image 1011 can be an image or model of the particular heart being analyzed or a representative model of a heart, either of which can be stored in computer memory. The dipole density information 1012 is shown for only a portion of the heart image 1011, which can be a user selectable portion. In some embodiments, the dipole density information 1012 can be displayed over substantially all of heart image 1011. In still other embodiments, the system, e.g., the electrical potential to surface charge/dipole density converter module 630, can be configured to render the dipole density information 1012 for a portion of the heart to which the system attributes abnormal behavior or indications, as diagnosed using the dipole (or surface charge) density information and/or voltage measurement information. The dipole density information 1012 and/or the heart image 1011 can represent a dynamic series of information sets, presented in a dynamic format (e.g. series of sequential frame of images). In some embodiments, dipole density information 1012 is updated throughout one or more cardiac cycles and presented on a static or dynamic heart image 1011, as described hereabove in reference to the method of FIG. 9. The dipole density information 1012 or other patient information included in display 1000 can be shown via a differentiating map, such as a display that differentiates values of information by varying a parameter selected from the group consisting of: color (e.g. a color map); contrast; brightness; hue; saturation level; and combinations thereof.

In some embodiments, display 1000 can include one or more other display areas provided in conjunction with the dipole (or surface charge) density area 1010. Such other display areas can be secondary display areas displaying information related to (e.g. related to and/or mathematically derived from) the dipole (or surface charge) density information in area 1010. As an example, a dipole (or surface charge) density time-plot display area 1014 can be provided that can be configured to dynamically show a plot of dipole density versus time at one or more heart chamber surface locations (one shown), which could correspond to dynamically changing dipole density information displayed in the dipole (or surface charge) density area 1010 (e.g. shown in synchrony with the information displayed in area 1010). In some embodiments, the surface locations are operator selectable.

The dynamically displayed information (e.g. area 1010, area 1014 and/or other dynamically displayed information displayed on display 1000) can preferably be played, paused, stopped, rewound, fast forwarded and/or otherwise controlled, using controls 1030. The dipole (or surface charge) density area 1010, dipole density time-plot area 1014 and/or other information of displayed on display 1000 can be independently controlled (e.g. via controls 1030) and/or temporally linked (e.g. temporally linked in static or dynamic views), in some embodiments. Another optional secondary display area could be an analysis display area 1016. In this embodiment, analysis area 1016 includes diagnostic information determined from the dipole density data. More specifically, in this case, the analysis area 1016 indicates an assessment of a heart condition and/or a cause of a heart condition (e.g., a rotor or other aberrant electrical activity resulting in an arrhythmia such as atrial fibrillation), at least in part, from the dipole density data. The indication could include one or more dipole density values and associated time stamps corresponding to dynamically displayed dipole density information in area 1010 that is automatically (e.g. by the system) and/or manually (e.g. by an operator of the system) marked for future viewing and/or assessment.

In various embodiments, the display 1000 can optionally include a second display area 1020 (or voltage measurement information area 1020), within which can be electronically rendered the voltage measurement information 1022 in conjunction with heart image 1011. Here, in this example, the measured voltages 1022 are projected or overlaid onto a surface of heart image 1011. Therefore, in accordance with aspects of the present invention, the system and display can overlay the distribution of dipole densities 1012 on the surface of heart image 1011 and project the measured voltages 1022 on the surface of the second heart image 1011, e.g., at the same time and in synchrony, as shown. As described hereabove, the dynamically displayed information in area 1020 can preferably be played, paused, stopped, rewound, fast forwarded and/or otherwise controlled, using controls 1030 (e.g. independently or in synchrony with area 1010).

In other embodiments, a static, single image of the heart can be shown and the user can have the ability to selectively overlay or project dipole density information, surface charge density information, and/or measured voltage measurement information on the single image. Therefore, display 1000 can include one or more controls (e.g. touch screen controls) responsive to user interaction to selectively toggle between the rendering of the dipole densities, surface charge densities, and/or voltage measurements on the image of the heart on the display screen (e.g. sequentially and/or simultaneously such as by using an overlay as described herebelow in reference to FIG. 11).

In some embodiments, display 1000 can include one or more other display areas (e.g. in conjunction with the voltage measurement information area 1020). Such other areas can be secondary areas displaying information related to the voltage measurement information area 1020. As an example, a voltage measurement time-plot 1024 can be provided that can be configured to dynamically show a plot of measure voltage versus time at one or more heart chamber surface locations (one shown), which could correspond to dynamically changing voltage measurement information displayed in the voltage measurement information area 1020— at one or more endocardial surface locations (e.g. synchronized to one or more operator selected surface locations) on the same time scale. That is, the time scale is the same as the time scale in the dipole density area 1010, and related secondary areas. In various embodiments, the user can select whether or not areas 1010 and 1020 are synchronized, and whether or not secondary areas are synchronized with the corresponding primary area 1010 and 1020. The dynamically displayed information can preferably be paused, stopped, rewound, and/or fast forwarded. The voltage measurement information area 1020 and voltage measurement information time-plot area 1024 and/or other information displayed on display 1000 can be independently controlled (e.g. via controls 1030) and/or temporally linked (e.g. temporally linked in static or dynamic views), in some embodiments.

Another optional secondary area could be an analysis area 1026. In this embodiment, analysis area 1026 includes diagnostic information determined from the voltage measurement information. More specifically, in this case, the analysis area 1026 indicates a heart condition (e.g., atrial fibrillation) determined, at least in part, from the voltage measurement information. The indication could include a voltage measurement information value and time stamp corresponding to the dynamically displayed voltage measurement information in area 1020.

In various embodiments, display 1000 can include one or more graphical mechanisms or other controls responsive to user interaction to change an orientation in two-dimensional (2D) or three-dimensional (3D) space of the image of the heart 1011 with overlaid dipole densities 1012. For example, one or more areas can include controls 1032 to zoom in and out or controls 1034 to rotate or turn the heart and overlaid information in an area (e.g., areas 1010 and 1020).

In various embodiments, as noted, the displays in areas 1010 and 1020 can be dynamically updated, where the system dynamically updates the distribution of dipole densities by altering visual characteristics thereof corresponding to changes in the dipole densities and/or measured voltages over time. Altering the visual characteristics can comprise altering at least one of color, intensity, hue, and shape of at least a portion of the rendered distribution of dipole densities 1012 and/or voltage measurement information 1022. The electronic rendering of the distribution of dipole densities 1012 on the display screen can be performed in real-time in response to voltage measurements obtained in real-time using the at least one electrode, as described above. The electronic rendering of the distribution of dipole densities on the display screen can be performed as post processing and/or analysis based on voltage measurements stored in at least one computer memory.

The display 1000 can include one or more graphical controls 1040 responsive to user interaction to record the user interactions with the display, e.g., on the same temporal time scale as the information displayed in areas 1010 and 1020, and related secondary areas (if any). For example, the system could be configured to receive audio inputs from a user interacting with the display 1000. Inputs that could be recorded and/or saved can include, but are not limited to: text inputs, audio inputs, and graphical inputs (or interactions). In such cases, a Practitioner Notes box 1042 could be included for textual inputs by a user and an audio input control 1044 can be included on enable and disable audio inputs. Controls 1030 can be used to play, rewind, and fast forward changes in the rendering of the distribution of dipole densities on the display screen over time, along with any recorded user interactions.

Figure 11:
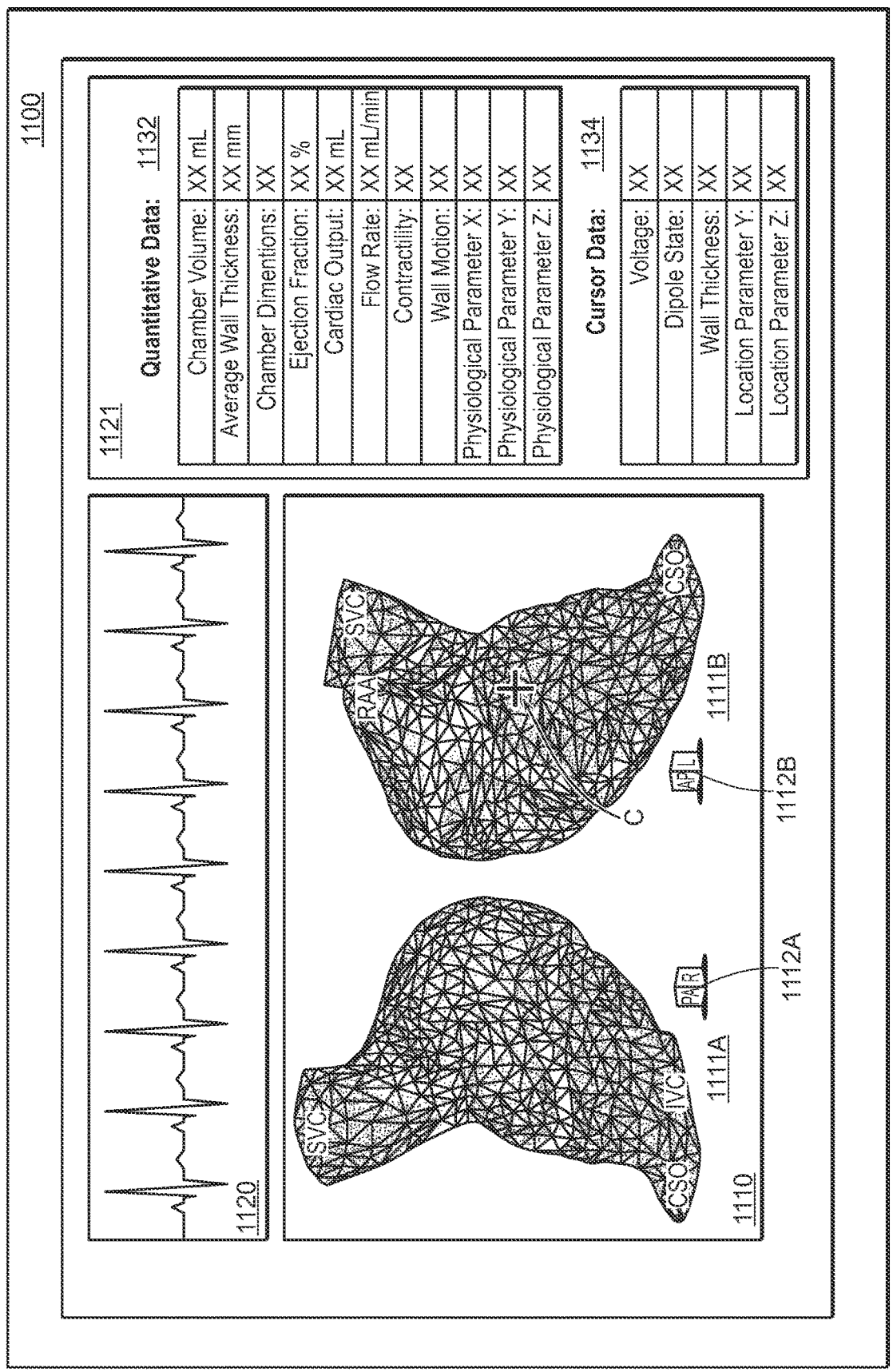
FIG. 11 is another embodiment of a user interface display of dipole and/or surface charge density information that can be generated on one or more devices, in accordance with aspects of the present invention.

FIG. 11 is another embodiment of a user interface display 1100 of dipole and/or surface charge density information that can be generated on one or more devices, in accordance with aspects of the present invention. The display of FIG. 11 can also include any of the interactive controls or features of the display of FIG. 10. Display 1100 includes area 1110 including one or more anatomical views of physiologic activity on one or more surfaces of a heart, such as the Right Posterior Oblique (RPO) view shown on the left and the Left Anterior Oblique (LAO) view shown on the right.

The anatomic images of area 1110 include a representation of sets of varying source and/or field data correlated in 3D space with surfaces of a heart and differentiated in magnitude with a color map, in the preferred embodiment. Alternatively or additionally, data can be differentiated with other graphical properties such as contrast, brightness, hue and/or saturation levels. These value-differentiating maps can represent the magnitude of field data (e.g. voltage data) and/or source data (e.g. dipole density or charge density data), e.g., at the same point in time in each view, simultaneously (e.g. via an overlay) or sequentially (e.g. by toggling the views). In some embodiments, an image of the heart is also shown, simultaneously or sequentially with the field and/or source data, as described hereabove in reference to FIG. 10. A heart image can comprise a static heart image (e.g. the image of the heart at the end of systole or diastole upon which field and/or source information is displayed), or a dynamic heart image such as a beating heart image. A static or dynamic heart image can be routinely updated, such as an image that is updated based on signals received from the ultrasound transducers of the present invention.

In some embodiments, field information (e.g. voltage information) and source information (e.g. dipole density or surface charge density information) is overlaid, such as when voltage data is displayed as a "bottom layer" and dipole density data is partially transparently displayed "on top" of the voltage data. This overlay could be done using an algorithm that mixes the overlaid colors (a "pigment-based" mixing), or by other methods, such as methods that affect brightness, contrast, or other techniques, known to those skilled in computer color manipulation and image processing. Different layers can be turned on and off, or toggled, color schemes modified, views changed, and so on, in response to an operator instruction or input or the presence of a condition determined by the computer, e.g., the cardiac information display controller 650 in FIG. 6. Each view can be controlled or changed independently or together—as a related pair. Next to each image 1111A, 1111B a 3D frame of reference icon 1112A, 1112B is displayed to aid the user in understanding the orientation of the heart image provided (e.g. anterior, posterior, medial, lateral and combinations of these, all standard orientations used in clinical imaging).

One or both of the views can display real (or near-real) time information that can dynamically change in response to changes in source and/or field information represented in or otherwise used in the views. For example, the information displayed in both views can dynamically change in response to measured, sensed, or calculated changes in represented source and/or field information, such as voltages, dipole density, surface charge density, temperature, pH, and so forth. Such changes can be embodied in changes in colors, hues, intensities, dynamic patterns, and so forth used in the views.

In this embodiment, in conjunction with the anatomical cardiac views, there is displayed an electrocardiogram (EKG or ECG) representing electrical activity of the heart in EKG area 1120. The EKG area 1120 and anatomical images 1111A, 1111B can dynamically change together, in various embodiments. EKG area 1120 translates the heart's electrical activity into line tracings on the display. In various embodiments, the EKG area 1120 can be turned on and off by the user.

In this embodiment, the display includes two tables 1132 and 1134 that include data gathered from the ultrasound transducers, electrodes, and/or other sensors of the present invention. The data (as shown in table 1132) could represent the chamber or system as a whole (Quantitative Data) and can also represent data (as shown in table 1134) specific to a cursor position or area selected by a user (e.g., a physician), e.g., by drawing a box with a cursor or placing the cursor over the image, as with cursor C (+) in FIG. 11.

In some embodiments, display 1100 further includes area 1121. Area 1121 can be configured to provide information provided by one or more of the ultrasound transducers, electrodes and/or other sensors of the present invention, such as ultrasound transducers 551, electrodes 541 of FIG. 5C described hereabove. Area 1121 can provide various patient information, such as calculated patient information (hereinafter "calculated information") as described herein. In some embodiments, area 1121 comprises quantitative and/or qualitative patient information related to a physiologic parameter of a patient that comprises calculated information determined by the sensor information (e.g. determined by mathematically processing the sensor information). Calculated information can comprise patient information selected from the group consisting of: cardiac chamber volume; cardiac wall thickness; average cardiac wall thickness; a cardiac chamber dimension; ejection fraction; cardiac output; cardiac flow rate; cardiac contractility; cardiac wall motion; other cardiac function information; voltage at a cardiac surface location; dipole state at a cardiac surface location; and combinations thereof. In these embodiments, voltage and/or dipole information can be calculated from signals recorded by one or more electrodes. In these embodiments, signals from one or more ultrasound transducers can be used to determine cardiac geometry information. Signals from one or more ultrasound transducers can be analyzed to determine the level or status one or more of: chamber volume; average wall thickness; chamber dimensions; ejection fraction; cardiac output; flow rate; contractility; wall motion; voltage; dipole state; and wall thickness. The information recorded by the ultrasound transducers can be used to dynamically define the geometric shapes of the chambers and walls of the heart, and one or more algorithms can be included to create quantitative measures of the these cardiac parameters, avoiding the need for: transesophageal and/or Transthoracic electrocardiography (TTE/TEE) and/or Intracardiac Echo (ICE) to measure wall motion such as abnormal wall motion; Functional MRI to measure contractility, cardiac output and/or stroke work; Positron Emission Tomography (PET Scan) and/or Single-Photon Emission Computed Tomography (SPECT Scan) to measure metabolic performance; Thermodilution and/or Impedance Volumetry catheters to measure cardiac output; and combinations of these. In some embodiments, area 1121 provides patient information selected from the group consisting of: blood pressure; heart rate; cardiac cycle length; pulse oximetry; respiration rate; and combinations of these. In some embodiments, the information provided in area 1121 and/or other areas of display 1100 is updated relatively continuously over time, e.g. at least every 10 seconds. In some embodiments, area 1121 includes an image of the heart, and cardiac information such as those listed above can be displayed in relation to the heart image (e.g. wall thickness displayed relative to the associated wall, chamber volume within the associated chamber, etc.). In some embodiments, quantitative information is displayed in numeric form (i.e. graphic elements of display 1100 comprising one or more numerals). Alternatively or additionally, quantitative information can be displayed with one or more graphic elements such as a line chart, bar chart and/or pie chart. In some embodiments, the information provided in area 1121 and/or other areas of display 1100 is updated on a periodic basis, such as once per minute, once per 5 minutes or once per 10 minutes. The information provided in area 1121 can be calculated information based on information collected over time, such as patient information that is summed, averaged, integrated, differentiated and/or otherwise mathematically processed by one or more algorithms. The patient information can comprise source information (e.g. dipole density of surface charge density information). In some embodiments, one or more algorithms find an average, a mean, a maximum level, a minimum level of one or more patient parameters. In some embodiments, one or more algorithms compare calculated information or other patient information to a threshold to produce calculated information. For example, if the level of a particular parameter exceeds a threshold (e.g. is over a maximum threshold or under a minimum threshold), the system can enter a new state such as an alert state. In some embodiments, after exceeding a threshold, the appearance of already displayed patient information can change, such as a color change (e.g. a change to red) and/or a font change (a change to italics or a change in boldness). Alternatively or additionally, an alert can be activated (e.g. an audible or tactile alert) to notify an operator of the system (e.g. a clinician) that a threshold has been exceeded.

Figure 12:
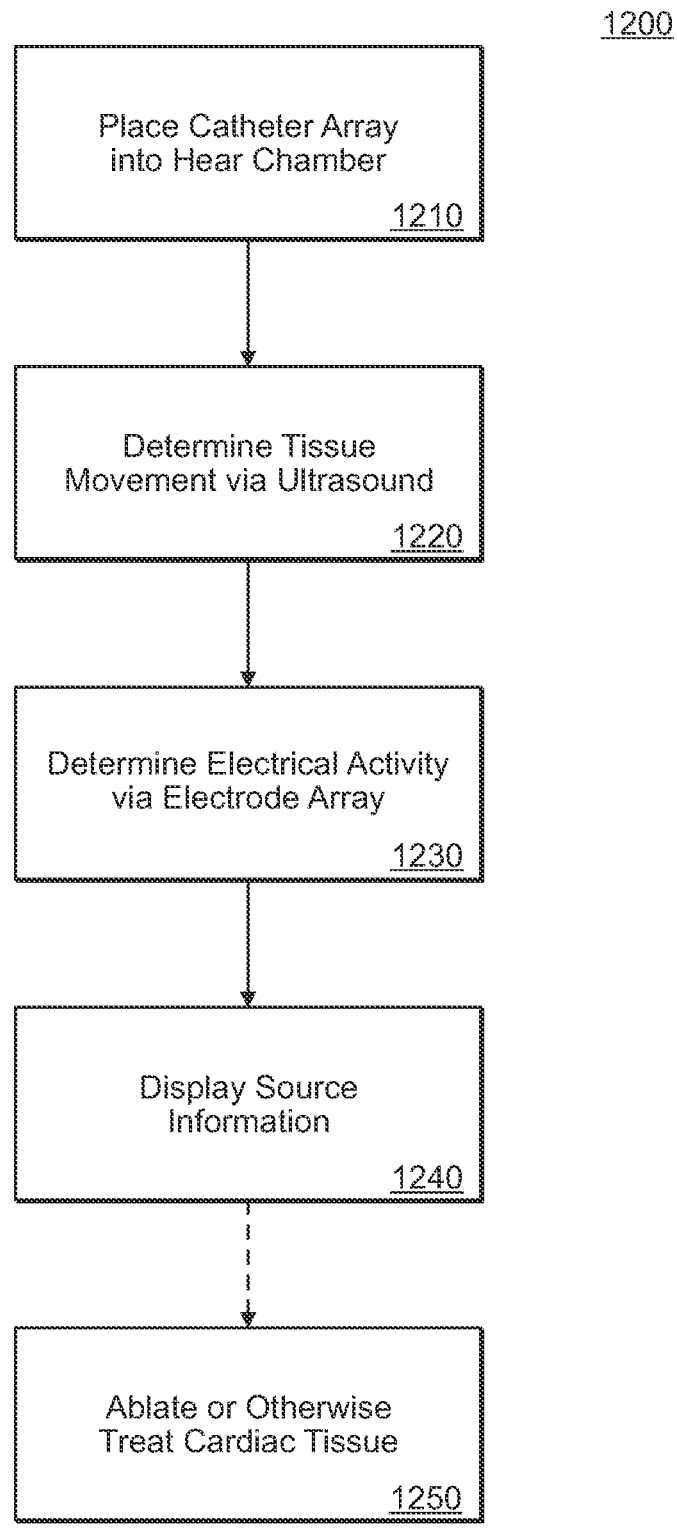
FIG. 12 is an example embodiment of a method of producing a model of a heart including the geometry of the cardiac surfaces, in accordance with aspects of the present invention.

Referring now to FIG. 12, a flow chart of an embodiment of a method for generating a model of a heart and providing a graphical representation of cardiac information on a display screen is illustrated. Method 1200 comprises displaying source information (e.g. dipole and/or surface charge density information) relative to a heart image on a display screen. Other information, such as field information (e.g. voltage information or other field information relative to the same or different cardiac locations) can be displayed, such as in a side-by-side arrangement, an overlay arrangement and/or an arrangement where the two sets of information are presented sequentially (e.g. toggled back and forth) in the same location (an "alternating arrangement"). In some embodiments, one or more cardiac parameters are quantified or otherwise determined utilizing the systems and devices of the present invention described hereabove. Cardiac parameters determined can include cardiac dimensions (e.g. chamber volume or wall thickness), cardiac function parameters (e.g. ejection fraction or cardiac output) and/or cardiac health, In Step 1210, the distal end of a catheter of the present invention is placed into one or more body locations, such as one or more cardiac chambers of a patient. The catheter comprises at least one electrode and at least one ultrasound element. The catheter includes one or more electrodes positioned on a distal portion of the catheter and configured to record electrical activity in tissue and/or deliver ablation energy. In Step 1220, anatomical information, such as tissue location, tissue movement, tissue thickness and/or tissue contour information can be determined via the at least one ultrasound element, typically an element configured to transmit and receive ultrasound waves as described hereabove. Alternatively or additionally, position and/or distance information can be recorded, such as position and/or distance information relative to one or more device components and/or tissue locations. In Step 1230, source information for one or more tissue locations can be determined via the at least one electrode, e.g. by recording voltage reading from multiple locations on and/or within the chamber of the heart and calculated the source information (e.g. calculating dipole density and/or surface charge density information as described hereabove). Steps 1220 and 1230 can be performed simultaneously or sequentially, in full or partial steps, and in any order. Either or both Steps 1220 and 1230 can be performed in two or more independent time periods.

In Step 1240, at least source information is provided to an operator of the system, such as via a display screen or in written form. In some embodiments, information is provided relative to a static image of the heart, such as an image at the end of systole or diastole. Alternatively or additionally, a dynamic set of heart images can be created representing a full cardiac cycle, or multiple cardiac cycles created over the course of a patient treatment procedure such as a cardiac ablation procedure performed to treat an arrhythmia such as atrial fibrillation. A dynamic set of source information can be presented on a display screen in synchrony with the dynamic set of heart images. In some embodiments, source information, field information, cardiac image information and/or cardiac parameter information are stored in memory, such as memory 680 of FIG. 6 described hereabove. In these embodiments, playback of stored information can be provided to an operator via the display screen.

In some embodiments, a further analysis of the ultrasound reflections recorded and the electrical charge information is performed. The further analysis can include determining a cardiac parameter selected from the group consisting of: cardiac chamber volume; cardiac wall thickness; average cardiac wall thickness; a cardiac chamber dimension; ejection fraction; cardiac output; cardiac flow rate; cardiac contractility; cardiac wall motion; other cardiac function information; voltage at a cardiac surface location; dipole state at a cardiac surface location; and combinations thereof, each of which can be provided to the operator on a display screen (e.g. information provided in relation to a certain tissue portion of the heart such as wall thickness information provided relative to the particular cardiac wall). Alternatively or additionally, the further analysis can include producing a diagnosis and/or prognosis of a tissue portion, which can similarly be provided to the operator on a display screen (e.g. information provided in relation to a certain tissue portion of the heart such as cardiac wall motion information provided relative to the particular cardiac wall).

For example, electrical information indicative of adequate electrical activity and anatomical information indicative of adequate tissue motion can correlate to the presence of healthy tissue. Additionally, electrical information indicative of adequate electrical activity and anatomical information indicative of inadequate tissue motion can correlate to presence of at least one of ischemic tissue or hibernating tissue. Conversely, electrical information indicative of inadequate electrical activity and anatomical information indicative of inadequate tissue motion can correlate to presence of scar tissue. Additionally, electrical information indicative of inadequate electrical activity and anatomical information indicative of inadequate tissue motion can correlate to the presence of a complete ablation, such as an ablation performed in a cardiac ablation performed to treat a cardiac arrhythmia (e.g. ablation of at least left atrial tissue to treat atrial fibrillation). In some embodiments, the complete ablation comprises a transmural ablation. In this use, the diagnosis and/or prognosis provided on the display screen can include the confirmation of the creation of a transmural lesion in the patient's heart tissue, such as when both tissue motion and electrical activity have been eliminated or decreased below a threshold.

More specifically, the following four cases can be determined to exist:
Case 1: Electrical and anatomical are adequate—Tissue is healthy,
Case 2: Electrical is adequate and anatomical is inadequate—Tissue is compromised,
Case 3: Electrical is inadequate and anatomical is adequate—Tissue is compromised, and
Case 4: Electrical and anatomical are both inadequate—Tissue necrosis.

The actual threshold for determining adequacy of electrical function of any one area of the heart is dependent upon many factors, including the degree of coordination of the activation pattern and the mass of the cells being activated. Additionally, this threshold will be different for each chamber of the heart as well as from smaller to larger patients. For example, a threshold of 0.5 mV can be appropriate, wherein an electrical potential smaller than 0.5 mV can be indicative of inadequate electrical function and an electrical potential at or larger than 0.5 mV can be indicative of adequate electrical function. In some embodiments, the thresholds are adjustable via one or more controls of the system of the present invention.

In some embodiments, tissue diagnostic algorithms can be configured to allow a clinician to assess the electrical integrity of cardiac cells. For example, the functional status of the cardiac cells can be assessed. In one embodiment, the electrical information comprises dipole density information. Additionally or alternatively, the electrical information can comprise at least one of repolarization or speed of repolarization information.

In some embodiments, tissue diagnostic algorithms use recordings from one or more ultrasound transducers (e.g. one or more ultrasound transducers on an array of the present invention) to produce calculated information representing a change in cardiac geometry. The calculated information can represent a measurement of heart contractility, and an undesired level of heart contractility and/or change in heart contractility can be identified and provided on a display. The calculated information can represent a measurement of volume of one or more cardiac chambers and an undesired level of cardiac chamber volume and/or change in cardiac chamber volume (e.g. left atrial enlargement that can occur during an atrial fibrillation procedure) can be identified and provided on a display. Numerous forms of patient information can be assessed, such as via a calculation that creates a measure of a change in patient information over a time period.

The information collected in Steps 1210 through 1230 and/or information derived from or otherwise calculated based on the collected information can be presented to an operator, such as when area 1121 or another area of display 1100 of FIG. 11 comprises the collected and/or calculated information.

The method can further comprise the optional Step 1250 comprising ablating or otherwise treating cardiac tissue, such as an ablation performed based upon source information, tissue diagnostic information and/or other information provided on a display screen. For example, the anatomical information comprising tissue thickness information and at least one of the magnitude of ablation energy or the time period in which ablation energy is delivered, is adjusted based on the tissue thickness information recorded by one or more ultrasound sensors. Alternatively or additionally, one or more other therapeutic procedures can be performed. In these therapeutic procedures, various calculated and/or collected information (e.g. anatomic, physiologic, therapeutic device and/or therapeutic procedure information) can be provided to an operator, such as when area 1121 or another area of display 1100 of FIG. 11 comprises the collected and/or calculated information. Such information includes but is not limited to: tissue thickness information; tissue contractility information; tissue density information; tissue temperature information; therapeutic device component temperature information (e.g. temperature of an electrode); duration of energy delivery information; and combinations of these. In some embodiments, changes in information are reflected by changes in the way information is displayed, such as density information for a tissue area changing from a grey or other color to a white or other non-grey color during ablation of that tissue area.

While the foregoing has described what are considered to be the best mode and/or other preferred embodiments, it is understood that various modifications can be made therein and that the invention or inventions may be implemented in various forms and embodiments, and that they may be applied in numerous applications, only some of which have been described herein. It is intended by the following claims to claim that which is literally described and all equivalents thereto, including all modifications and variations that fall within the scope of each claim.

What is claimed is:

1. A method of generating a graphical representation of cardiac information on a display screen, comprising:
    acquiring an anatomical model of the heart including at least one cardiac chamber, including updating the anatomical model at least once every 30 minutes;
    electronically determining multiple sequential data sets of source information corresponding to cardiac activity at multiple cardiac locations of the at least one cardiac chamber, the source information comprising dipole density information determined for a point on a surface of the heart, surface charge information, temperature information, pH information, or a combination of two or more thereof,
    wherein the multiple sequential data sets of source information are electronically determined at least once per second;
    electronically rendering the anatomical model of the heart on the display screen and then rendering an updated anatomical model of the heart on the display screen; and
    electronically rendering calculated information based on the data sets of source information in relation to the multiple cardiac locations of the anatomical model or the updated anatomical model of the heart on the display screen, including:
        rendering the calculated information as an instantaneous map of cardiac activation across the entire at least one cardiac chamber that graphically differentiates values of the calculated information overlaid on the anatomical model.

2. The method of claim 1, wherein the anatomical model is updated at least once every minute.

3. The method of claim 1, wherein the anatomical model is updated at least once every second.

4. The method of claim 1, wherein the anatomical model is updated at least once every 100 milliseconds.

5. The method of claim 1, wherein the anatomical model is updated at least 30 times per second.

6. The method of claim 1, wherein the anatomical model is created using data from a CT and/or an MIll scan.

7. The method of claim 1, wherein the anatomical model is created using signals from at least one ultrasound transducer.

8. The method of claim 7, wherein the at least one ultrasound transducer is positioned within the heart chamber.

9. The method of claim 1, wherein the anatomical model of the heart comprises a static model of the heart.

10. The method of claim 1, wherein the anatomical model of the heart comprises a dynamic model of the heart beating.

11. The method of claim 1, wherein the multiple sequential data sets of source information represent a dynamic series of information sets.

12. The method of claim 11, wherein the dynamic series of information sets is updated throughout one or more cardiac cycles.

13. The method of claim 1, wherein the source information is data representing, at a location in 3D space, a physical property or properties discrete to the specific location in 3D space.

14. The method of claim 1, wherein the source information comprises dipole density data determined for a point on the surface of the heart.

15. The method of claim 1, wherein electronically determining multiple sequential data sets of source information comprises recording signals from at least one electrode.

16. The method of claim 15, wherein the at least one electrode comprises multiple electrodes.

17. The method of claim 16, wherein the multiple electrodes are mounted to an expandable array constructed and arranged for placement within a cardiac chamber.

18. The method of claim 1, wherein the calculated information is presented in the form of, or using, a differentiating map.

19. The method of claim 18, wherein the differentiating map comprises a map of value differentiating parameters including:
    color;
    contrast;
    brightness;
    hue;
    saturation level; or
    combinations of two or more thereof.

20. The method of claim 1, comprising rendering a data set of field information on the display screen.

21. The method of claim 20, comprising displaying the data set of field information in an alternating arrangement with the data set of source information.

22. The method of claim 1, further comprising:
    acquiring updated anatomical data from one or more ultrasound transducers located within the at least one cardiac chamber; and
    updating the anatomical model based, at least in part, on the updated anatomical data.

* * * * *

UNITED STATES PATENT AND TRADEMARK OFFICE
CERTIFICATE OF CORRECTION

PATENT NO. : 11,931,157 B2
APPLICATION NO. : 17/578522
DATED : March 19, 2024
INVENTOR(S) : Christoph Scharf et al.

It is certified that error appears in the above-identified patent and that said Letters Patent is hereby corrected as shown below:

In the Claims

Column 40, Line 2, Claim 6, replace the word "Mill" with --MRI--.

Signed and Sealed this
Twenty-eighth Day of May, 2024

Katherine Kelly Vidal
*Director of the United States Patent and Trademark Office*